(12) United States Patent
Aranda Almansa et al.

(10) Patent No.: US 11,214,529 B2
(45) Date of Patent: Jan. 4, 2022

(54) PRODUCTION AND ISOLATION OF MONOCYCLIC AROMATIC COMPOUNDS FROM A GASIFICATION GAS

(71) Applicant: Nederlandse Organisatie voor toegepast-natuurwetenschappelijk Onderzoek TNO, The Hague (NL)

(72) Inventors: Guadalupe Aranda Almansa, Petten (NL); Alexander Bos, Petten (NL); Berend Joost Vreugdenhil, Petten (NL)

(73) Assignee: Nederlandse Organisatie voor toegepast-natuurwetenschappelijk Onderzoek TNO, 's-Gravenhage (NL)

( * ) Notice: Subject to any disclaimer, the term of this patent is extended or adjusted under 35 U.S.C. 154(b) by 232 days.

(21) Appl. No.: 16/611,871

(22) PCT Filed: May 14, 2018

(86) PCT No.: PCT/NL2018/050315
§ 371 (c)(1),
(2) Date: Nov. 8, 2019

(87) PCT Pub. No.: WO2018/208163
PCT Pub. Date: Nov. 15, 2018

(65) Prior Publication Data
US 2021/0155563 A1    May 27, 2021

(30) Foreign Application Priority Data
May 12, 2017 (NL) .................................. 2018908

(51) Int. Cl.
*C07C 2/76* (2006.01)
*B01D 53/00* (2006.01)
(Continued)

(52) U.S. Cl.
CPC ............. *C07C 2/76* (2013.01); *B01D 53/002* (2013.01); *B01D 53/1418* (2013.01);
(Continued)

(58) Field of Classification Search
CPC .. C07C 2/76; C07C 7/005; C07C 7/10; C07C 7/11; C07C 2/42; C07C 4/06;
(Continued)

(56) References Cited

U.S. PATENT DOCUMENTS 3,972,958 A * 8/1976 Garwood ............ C07C 29/1518
                                                      208/414
4,025,318 A * 5/1977 Moody .................. C10G 47/00
                                                       48/213
(Continued)

FOREIGN PATENT DOCUMENTS

CN      106117003      11/2016
EP       0050021        4/1982
(Continued)

OTHER PUBLICATIONS

Rabou et al: "Tar in Biomass Producer Gas, the Energy research Centre of The Netherlands (ECN) Experience: An Enduring Challenge", Energy Fuels 2009, 23, p. 6189-6198.

*Primary Examiner* — Ali Z Fadhel
(74) *Attorney, Agent, or Firm* — N.V. Nederlandsch Octrooibureau; Catherine A. Shultz; Katelyn J. Bernier

(57) ABSTRACT

The present invention concerns a process and system for producing and isolating a fraction of monocyclic aromatic compounds from a gasification gas. The process comprises (a) contacting the gas with a catalyst capable of converting ethylene and possibly other unsaturated hydrocarbons into monocyclic aromatic compounds; and (b) isolating monocyclic aromatic compounds from the gas originating from step (a). The present invention is ideally suited for treatment (Continued)

of gas from coal, biomass or waste gasification, which comprises substantial amounts of ethylene as well as monocyclic aromatic compounds. Treatment according to the invention first converts the ethylene into further monocyclic aromatic compounds, and the entire fraction of monocyclic aromatic compounds is isolated to obtain a valuable product.

15 Claims, 18 Drawing Sheets

(51) Int. Cl.
| | |
|---|---|
| B01D 53/14 | (2006.01) |
| B01J 19/24 | (2006.01) |
| C07C 7/00 | (2006.01) |
| C07C 7/10 | (2006.01) |
| C07C 7/11 | (2006.01) |
| C07C 2/42 | (2006.01) |
| C07C 4/06 | (2006.01) |

(52) U.S. Cl.
CPC ..... B01D 53/1425 (2013.01); B01D 53/1487 (2013.01); B01J 19/24 (2013.01); C07C 7/005 (2013.01); C07C 7/10 (2013.01); C07C 7/11 (2013.01); B01D 2252/20 (2013.01); C07C 2/42 (2013.01); C07C 4/06 (2013.01); C07C 2529/40 (2013.01)

(58) Field of Classification Search
CPC ..... C07C 2529/40; C07C 15/04; C07C 15/06; C07C 15/08; C07C 15/073; C07C 2529/06; B01D 53/002; B01D 53/1418; B01D 53/1425; B01D 53/1487; B01D 2252/20; B01J 19/24
See application file for complete search history.

(56) References Cited

U.S. PATENT DOCUMENTS

| | | | |
|---|---|---|---|
| 2009/0156870 A1 | 6/2009 | Lauritzen et al. | |
| 2011/0011721 A1* | 1/2011 | Champagne | C10L 3/00 201/20 |
| 2014/0206914 A1* | 7/2014 | Gonzalez | C07C 1/24 585/253 |
| 2014/0349361 A1* | 11/2014 | Blommel | C12P 7/10 435/166 |
| 2015/0137043 A1* | 5/2015 | Chen | C10G 69/06 252/373 |

FOREIGN PATENT DOCUMENTS

| | | |
|---|---|---|
| EP | 0178847 | 4/1986 |
| GB | 2063291 | 6/1981 |
| WO | 03018723 | 3/2003 |
| WO | 2008010717 | 1/2008 |
| WO | 2014051419 | 4/2014 |

* cited by examiner

PRODUCTION AND ISOLATION OF MONOCYCLIC AROMATIC COMPOUNDS FROM A GASIFICATION GAS

FIELD OF THE INVENTION

The present invention relates to an improved process and system for obtaining a fraction of monocyclic aromatic compounds from a product gas of a gasification process, preferably a coal, biomass or waste gasification process.

BACKGROUND ART

An energy gas (also called product gas or gasification gas) is a combustible gas mixture that comprises compounds such as $H_2$, CO, $CH_4$ and other lower hydrocarbons (e.g. $C_1$-$C_5$ alkanes and $C_1$-$C_5$ alkenes). Such gases typically originate from gasification or pyrolysis from solid fuels, such as coal, biomass or waste and may be used in the production of e.g. heat, electricity, Fischer-Tropsch Diesel, substitute natural gas (SNG) and the like. Biomass is currently the only renewable carbon source which can potentially replace fossil fuels for the production of fuels and chemicals. Biomass and waste gasification usually takes place at low-medium temperatures (750-900° C.), so that the product gas contains, besides CO, $H_2$ and $CO_2$, compounds such as $CH_4$ and other lower hydrocarbons (e.g. $C_1$-$C_4$ alkanes and $C_1$-$C_4$ alkenes), monocyclic aromatic compounds (e.g. benzene, toluene, xylene (BTX)), and tars. Some of these compounds (e.g. ethylene, BTX) have a harmful effect in downstream processes and at the same time have a high economic value, even higher than the final product in e.g. bio-SNG processes. Therefore, the recovery of these valuable compounds from product gas in co-production schemes offers a considerable improvement with respect to their costly conversion to syngas. Despite the high value of bio-ethylene, there is a technical challenge in its separation from the remaining components in product gas. Conventional cryogenic technology is energy-intensive and cannot be economically applied in gasification applications.

Gases obtained by gasification or pyrolysis typically contain compounds such as $H_2$, $CO_2$, CO and lower hydrocarbons, together with further organic compounds such as monocyclic aromatic compounds as well as tar-like polycyclic aromatic components. Gasification or pyrolysis of biomass and waste yields significant amount of aromatic compounds. In biomass, large structures of aromatic moieties (e.g. lignin) are typically present. To be able to use the energy gas in the applications mentioned above, tars and further aromatic compounds need to be removed from the gas. Purifying gases such as energy gases from tars is typically accomplished by contacting the (energy) gas with a washing liquid, during which tars are removed from the gas and absorbed in the washing liquid, which may then be stripped to remove the tars from the washing liquid (see Rabou et al., *Energy Fuels,* 2009, 23, 6189-6198). Conventional process for purifying gases however do not sufficiently remove the lowest, i.e. monocyclic, aromatic compounds, such as benzene, toluene and xylene, from the gas, which thus needs to be further treated (e.g. steam reforming) to convert these compounds to gaseous fuels such as $H_2$, $CO_2$, CO and $CH_4$.

WO 03/018723 describes a process for removing tars with an aromatic hydrocarbon based washing liquid from a synthesis gas obtained during gasification of biomass. Gasification gas is subjected to a two-step cleaning treatment for removing tars. In a first step the gas is condensed in a washing liquid which is a hydrocarbon oil, wherein heavy tars (such as $C_{18}$ and higher) are removed. In a second stage, a different washing liquid is used for absorption of the remaining tars (typically $C_{9-18}$) in an absorption column. A further process using hydrocarbon oil as washing liquid is known from WO 2008/010717. The use of hydrocarbon oils for removing tars has some disadvantages, such as a limited stability at high temperatures and in the presence of water and oxidative agents, resulting in degradation and loss of oil due to the significant volatility of the hydrocarbons. As a result, the washing liquid and equipment are contaminated and the process must be interrupted at regular intervals for exchange of the washing liquid and cleaning of equipment.

U.S. Pat. No. 5,772,734 discloses the use of a wide variety of organic washing liquids, including low-viscosity silicone oils, light minerals oils and glycol ether especially triethylene glycol dibutyl ether for removing organic compounds such as chlorinated hydrocarbons or aromatic hydrocarbons from industrial gas streams. WO 2014/051419 describes a process for the purification of a gas stream, wherein the gas stream is contacted with a liquid organic polysiloxane at a temperature of 30-150° C. Such contacting results in removal of tar-like components in a single step. Light aromatic compounds such as benzene are not sufficiently removed by the contacting step, and the benzene that is removed is obtained in a mixture with the tar-like components (heavy aromatic compounds). Separation of such mixtures of light and heavy aromatic compounds is not economically feasible, causing huge waste streams and loss of the fraction of light aromatic compounds such as benzene as a valuable product. Similarly, US 2017/0044446 discloses a process wherein ethylene from refinery off gases is converted into C5+ olefins, naphthenics and aromatic compounds, and these compounds are isolated in a single batch, containing a mixture including both monocyclic and polycyclic aromatic compounds.

Ethylene accounts for a relatively small fraction of about 3.5 vol. % of the total volume of the product gas from biomass gasification. However, its calorific value accounts for a relatively high fraction of about 16% of the gas. Moreover, the ethylene content is significantly higher in product gas from waste gasification. Ethylene has a harmful effect in synthesis processes as a coking precursor of catalysts. However, separation of ethylene is technically challenging. Light olefins and alkanes are commonly separated through costly high-pressure cryogenic separation (see e.g. Zimmerman and Walzl, Ethylene in *Ullmann's Encycl. Ind. Chem.* 2000; Eldridge, *Ind. Eng. Chem. Res.* 1993, 32, 2208-2212; Safarik and Eldridge, *Ind. Eng. Chem. Res.* 1998, 37, 2571-2581; Faiz and Li, *J. Desal.* 2012, 287, 82-97). Moreover, ethylene and ethane have similar boiling points; therefore, the separation of ethane and ethylene is challenging, and requires expensive fractionation steps (Faiz and Li, *J. Desal.* 2012, 287, 82-97). The main disadvantage of the low-temperature separation of olefins from gases is the high capital and energy cost. Low-temperature separation is considered economically feasible only when the olefin concentration in the feed gas is at least 20 wt % (U.S. Pat. No. 4,401,450). Alternative processes for the separation of olefins and alkanes, such as extractive distillation, adsorption, absorption, membrane separation, and combinations thereof (Eldridge, *Ind. Eng. Chem. Res.* 1993, 32, 2208-2212; Faiz and Li, *J. Desal.* 2012, 287, 82-97), present technical challenges, such as contamination or poisoning, water content control, chemical and thermal stability, and fouling.

In view of the above, there remains a need in the art for efficient and selective separation of the BTX fraction from gasification gases. Further, there remains a need in the art for utilizing the ethylene present in product gas without the need for inefficient separation nor the problematic conversion into $CO$, $H_2$, $CO_2$ and/or $CH_4$. The present invention provides in both these needs.

SUMMARY OF THE INVENTION

The present invention concerns a process and system for producing and isolating a fraction of monocyclic aromatic compounds from a product gas of a gasification process. The process comprises:
(a) contacting the gas with a catalyst capable of converting ethylene into monocyclic aromatic compounds;
(b) isolating monocyclic aromatic compounds from the gas originating from step (a).

The system according to the invention is designed to perform the process according to the invention. The system is modular and comprises:
(a) an ethylene conversion module for converting ethylene into monocyclic aromatic compounds, comprising a gas inlet (a1) for receiving the incoming gas, a catalyst (a2) capable of converting ethylene into monocyclic aromatic compounds and a gas outlet (a3) for discharging a gas enriched in monocyclic aromatic compounds;
(b1) an absorbing unit comprising a gas inlet (b11) for receiving the gas enriched in monocyclic aromatic compounds, a liquid inlet (b12) for receiving a washing liquid, a gas outlet (b14) for discharging a purified gas and a liquid outlet (b15) for discharging a spent washing liquid; and (b2) a stripping unit, comprising a liquid inlet (b21) for receiving the spent washing liquid, a gas inlet (b22) for receiving a stripping gas, a gas outlet (b23) for discharging a loaded stripping gas and a liquid outlet (b24) for discharging a stripped washing liquid.

Herein, outlet (a3) is in fluid connection with inlet (b11), outlet (b15) is in fluid connection with inlet (b21) and preferably outlet (b24) is in fluid connection with inlet (b12).

The present invention is ideally suited for treatment of gas from coal, biomass or waste gasification, which comprises substantial amounts of ethylene as well as monocyclic aromatic compounds. Treatment according to the invention first converts the ethylene into further monocyclic aromatic compounds, and the entire fraction of monocyclic aromatic compounds is isolated to obtain a valuable product. In addition, a product gas cleared from ethylene as well as monocyclic aromatic compounds is obtained, which is ideally suited for the manufacture of (bio-)SNG or other biofuels.

LIST OF PREFERRED EMBODIMENTS

1. A process for producing a fraction of monocyclic aromatic compounds from a product gas of a gasification process, comprising:
   (a) contacting the gas with a catalyst capable of converting ethylene into monocyclic aromatic compounds;
   (b) isolating monocyclic aromatic compounds from the gas originating from step (a).
2. The process according to embodiment 1, wherein the gasification process involves the gasification of coal, biomass or waste.
3. The process according to embodiment 1 or 2, wherein the isolating of step (b) is performed by
   (b1) contacting the gas originating from step (a) with a washing liquid, at a temperature of 15-60° C., to obtain the purified gas and a spent washing liquid;
   (b2) contacting the spent washing liquid with a stripping gas comprising steam, to obtain a loaded stripping gas comprising monocyclic aromatic compounds and a stripped washing liquid; and
   (b3) separating the monocyclic aromatic compounds from the loaded stripping gas obtained in step (b2) to obtain a composition comprising monocyclic aromatic compounds.
4. The process according to embodiment 3, wherein the stripping gas comprises at least 95 vol. % steam.
5. Process according to embodiments 3 or 4, wherein step (c) involves condensation of the loaded stripping gas to obtain an immiscible liquid composition comprising water and monocyclic aromatic compounds, collection of the composition in a vessel and liquid-liquid separation thereof.
6. The process according to any one of the preceding embodiments, wherein the washing liquid comprises an organic polysiloxane.
7. The process according to any one of the preceding embodiments, wherein the monocyclic aromatic compounds include one or more selected from benzene, toluene, xylenes and ethylbenzene.
8. The process according to any one of the preceding embodiments, wherein the catalyst capable of converting ethylene into monocyclic aromatic compounds comprises a zeolite, preferably a ZSM-5 zeolite, either unpromoted or preferably promoted with Ga, Zn and/or Mo.
9. The process according to any one of the preceding embodiments, wherein step (a) is performed at a temperature of 250-650° C., preferably 450-520° C.
10. The process according to any one of the preceding embodiments, wherein the gas that is subjected to step (a) comprises ethylene and preferably (i) 5-30 vol % $CH_4$; (ii) 1-15 vol % $C_2H_x$, wherein x=2, 4 or 6; (iii) 1-10 vol. % $C_yH_z$, wherein y=3, 4 or 5 and z=(2y−2), (2y) or (2y+2); (iv) 10-60 vol % $H_2$; (v) 5-50 vol % CO; and (vi) 5-50 vol % $CO_2$, based on total dry volume.
11. Process according to any one of the preceding embodiments, wherein tar-like components are removed from the gas prior to step (a), by:
    (c1) contacting the gas with a pre-washing liquid at a temperature of 60-150° C., to obtain a detarred gas which is fed to step (a) and a spent pre-washing liquid; and
    (c2) contacting the spent pre-washing liquid with a tar stripping gas, to obtain a loaded tar stripping gas and a stripped pre-washing liquid.
12. Process according to any one of the preceding embodiments, wherein the gas is subjected to water removal prior to step (a), preferably by means of a condenser.
13. Modular system for performing the process according to any one of embodiments 1-12, comprising:
    (a) an ethylene conversion module for converting ethylene into monocyclic aromatic compounds, comprising a gas inlet (a1) for receiving the gas, a catalyst (a2) capable of converting ethylene into monocyclic aromatic compounds and a gas outlet (a3) for discharging a gas enriched in monocyclic aromatic compounds;
    (b1) an absorbing unit comprising a gas inlet (b11) for receiving the gas enriched in monocyclic aromatic compounds, a liquid inlet (b12) for receiving a washing liquid, a gas outlet (b14) for discharging a purified gas and a liquid outlet (b15) for discharging a spent washing liquid; and (b2) a stripping unit, comprising a liquid inlet (b21) for receiving the spent washing liquid, a gas inlet (b22) for receiving a stripping gas, a gas outlet (b23) for discharging a loaded stripping gas and a liquid outlet (b24) for discharging a stripped washing liquid, wherein outlet (a3) is in fluid connection with inlet (b11), outlet (b15) is in fluid connection with inlet (b21) and preferably outlet (b24) is in fluid connection with inlet (b12).

14. Modular system according to embodiment 13, further comprising:

(b3) a separating module, comprising a gas inlet (b31) for receiving the loaded stripping gas, means (b32) for separating the monocyclic aromatic compounds from the stripping gas, an outlet (b33) for discharging a cleared stripping gas, and an outlet (b34) for discharging the monocyclic aromatic compounds, wherein outlet (b23) is in fluid connection with inlet (b31) and outlet (b33) is preferably in fluid connection with inlet (b22).

15. Modular system according to embodiment 13 or 14, further comprising:

(c1) a pre-washing unit comprising a gas inlet (c11) for receiving a gas comprising tar-like components and monocyclic aromatic compounds, a liquid inlet (c12) for receiving a pre-washing liquid, a gas outlet (c14) for discharging a detarred gas and a liquid outlet (c15) for discharging a spent pre-washing liquid; and (c2) a tar stripping unit, comprising a liquid inlet (c21) for receiving the spent pre-washing liquid, a gas inlet (c22) for receiving a tar stripping gas, a gas outlet (c23) for discharging loaded tar stripping gas and a liquid outlet (c24) for discharging a stripped pre-washing liquid.

wherein outlet (c14) is in fluid connection with inlet (a1), outlet (c15) is in fluid connection with inlet (c21) and preferably outlet (c24) is in fluid connection with inlet (c12).

DETAILED DESCRIPTION

The present invention relates to an improved process and system for obtaining a fraction of monocyclic aromatic compounds from a gasification gas (which can be produced from coal, biomass or waste), and at the same time purifying said gas. The process according to the invention on the one hand purifies the incoming gas in the sense that ethylene (as well as other unsaturated hydrocarbons) and monocyclic aromatic compounds are removed from the gas, and at the same time produces a fraction of monocyclic aromatic compounds, a valuable co-product of the process according to the invention. A typical application of the incoming gas, particularly in the form of a (biomass and/or waste) gasification product gas, is the manufacture of (bio-)SNG, although the invention can be also applied in other end applications of the gas. As such, the process according to the invention increases the value of the incoming gas, since ethylene is converted into higher-value liquid product, the monocyclic aromatic compounds, without the need of costly infrastructure for transport of gas-phase ethylene, and which is easily retrofitted into existing gasification facilities.

Process

The process according to the invention is for producing a fraction of monocyclic aromatic compounds from a product gas, comprising (a) contacting the gas with a catalyst capable of converting ethylene and other unsaturated hydrocarbons into monocyclic aromatic compounds; and (b) isolating monocyclic aromatic compounds from the gas originating from step (a). The process may also be referred to as a process "for purifying a product gas", "for producing and isolating a fraction of monocyclic aromatic compounds" or "for producing a fraction of monocyclic aromatic compounds and a purified product gas".

The gas to be treated in the process according to the invention is also referred to as the "incoming gas", the "product gas", the "gasification gas" or just "the gas". The term "permanent gas" refers to those compounds that remain gaseous throughout the entire process.

The Incoming Gas

The incoming gas, also referred to as the gas to be purified, can be comprised of any gaseous small molecules such as hydrogen, nitrogen, methane, ethylene, optionally further small hydrocarbons (up to 5 carbon atoms), carbon monoxide and carbon dioxide. The incoming gas comprises ethylene and at least one further component selected from hydrogen, methane and carbon monoxide, preferably at least two or even all three of hydrogen, methane and carbon monoxide. The incoming gas may further contain one or more components selected from carbon dioxide, other lower hydrocarbons (e.g. ethane, $C_3$, $C_4$ and $C_5$ hydrocarbons), larger alkanes and olefins (e.g. up to 6 or even 7 carbon atoms), inert gases (e.g. nitrogen) and water. The incoming gas may also be referred to as "energy gas", "gasification gas" or "product gas".

In a preferred embodiment, the incoming gas further comprises monocyclic aromatic compounds, although their presence is not essential for the functioning of the process according to the invention. In case monocyclic aromatic compounds are already present in the incoming gas, they are efficiently removed from the gas in step (b), together with the monocyclic aromatic compounds that are produced in step (a). However, in case they are not present in the incoming gas, step (b) will still afford the monocyclic aromatic compounds produced in step (a).

In the context of the present invention, monocyclic aromatic compounds include both compounds having only carbon atoms in the aromatic ring(s) (i.e. carbocycles) as well as heteroaromatic compounds comprising at least one non-carbon ring atom (i.e. heterocycles), typically selected from N, O and S. The monocyclic aromatic compounds present in the incoming gas typically have a boiling point below 200° C. (when determined at ambient pressure), preferably below 120° C., most preferably below 100° C. Typically, the monocyclic aromatic compounds include at least one of benzene, toluene and xylene, more preferably at least benzene, most preferably all of benzene, toluene and xylene, which are together referred to as BTX. In addition, further low-boiling monocyclic aromatic compounds may be present, such as ethylbenzene, styrene, cresol and thiophene. In case the gas, such as gas originating from a gasification or pyrolysis, comprises aromatic compounds having a boiling point in the range of 100-300° C., these compounds may be present in the gas subjected to step (a) or they may be removed in a pre-washing or pre-cleaning step prior to step (a). Examples of such aromatic compounds include phenol, cresols, ethylbenzene, styrene, cumene, naphthalene and the like.

Where monocyclic aromatic compounds are preferably present in the incoming gas, the content of high boiling aromatic compounds (tars) is preferably kept low. In other words, the gas being subjected to step (a) is conveniently lean in tar-like components. In one embodiment, the gas subjected to step (a) is substantially free from tar-like components. In case the incoming gas contains substantial amounts of tar-like components, they are beneficially removed from the incoming gas prior to step (a). In that case, the process according to the invention preferable comprises a step (c) of removing tar-like components from the gas. Tar-like components are aromatic compounds having a boiling point above 300° C. (when determined at ambient pressure), preferably above 250° C., most preferably above 200° C. Aromatic compounds that are classified as tar-like in the context of the present invention usually are bicyclic, tricyclic and tetracyclic aromatic compounds having 9-18 aromatic ring atoms, typically 9-18 carbon atoms. These are largely carbocyclic (i.e. all-carbon aromatic rings), but heterocyclic compounds such as indoles, (iso)quinolines and chromenes, may also be present. Examples of (polycyclic) aromatic compounds which are classified as tar-like components include indene, naphthalene, quinoline, isoquinoline, 2-methylnaphthalene, 1-methyl-naphthalene, biphenyl, ethenyl-naphthalene, acenaphthylene, acenaphthene, fluorene, anthracene, phenanthrene, fluoranthene, pyrene, aceanthrylene, benzoanthracenes and chrysene. In addition to the 9-18 ring atom components, heavier aromatic compounds, e.g. up to 24 ring atoms or even larger are also classified as tar-like in the context of the present invention. Examples include benzofluoranthenes, benzopyrenes, perylene, picene, benzoperylenes, indenoperylenes, dibenzoanthracenes, benzoperylenes, coronene, etc. Their content in the gas subjected to step (a) is preferably kept low and/or they are all effectively removed in step (c). In case the incoming gas stream contains substantial levels of tar-like components having more than 18 ring atoms, in particular if it contains components of more than 24 ring atoms, a pre-cleaning step is preferably incorporated in the present process, as further described below. Lighter aromatic compounds such as phenol, cresols, ethylbenzene, styrene, cumene and the like may also be substantially absent in the gas subjected to step (a), e.g. by removal thereof in step (c), although they may also be present in the incoming gas and removed in step (b). In case step (c) is performed in the process according to the invention, it depends on the exact conditions thereof whether or not these are removed in step (c). If so, those are then included in the tar-like component fraction removed in step (c). However, they may also be present in the gas subjected to step (a), either when step (c) is not performed or in case the conditions of step (c) are such that these compounds are not removed. As such, these compounds will be removed in step (b) and are thus included in the fraction of aromatic compounds obtained in step (b).

Typically, the gasification gas stream comprises at least one of hydrogen, CO and $C_{1-5}$ alkanes, preferably at least one of hydrogen, CO and methane. The feeding gas may also contain larger alkanes (e.g. up to 6 or even 7 carbon atoms) and olefins (including ethylene, acetylene and other $C_3$-$C_5$ unsaturated species). For example, the gas may comprise hydrogen, carbon monoxide, carbon dioxide, methane, ethylene, nitrogen, and water (vapour). The gas is in particular an energy gas, product gas or a synthesis gas, typically containing one or more of hydrogen, carbon monoxide, and methane, in addition to varying levels of nitrogen, carbon dioxide and/or water, and sometimes ammonia, HCl and/or hydrocarbons other than methane. The presence of at least one of CO and $CO_2$, preferably both CO and $CO_2$, in the incoming gas that is subjected to step (a) is preferred, since the inventors have found hints that these species may contribute to stabilize the catalyst.

In one embodiment, the incoming gas that is subjected to step (a) comprises: (i) 5-30 vol % $CH_4$, preferably 10-25 vol % $CH_4$, most preferably 12-20 vol % $CH_4$; (ii) 1-15 vol % $C_2H_y$, preferably 2-10 vol % $C_2H_y$, most preferably 3-8 vol % $C_2H_x$, wherein x=2, 4 or 6; (iii) 1-10 vol % $C_yH_z$, preferably 1-5 vol % $C_yH_z$, wherein y=3, 4 or 5 and z makes up for the open valencies of carbon, typically z=(2y−2), (2y) or (2y+2); (iv) 10-60 vol % $H_2$, preferably 20-50 vol % $H_2$, most preferably 25-40 vol % $H_2$; (v) 5-50 vol % CO, preferably 15-40 vol % CO, most preferably 20-35 vol % CO; and (vi) 5-50 vol % $CO_2$, preferably 10-40 vol % $CO_2$, most preferably 15-30 vol % $CO_2$. Further, there are typically minor amounts of monocyclic aromatic compounds present, such as 0.1-5 vol % benzene, preferably 0.5-4 vol % benzene, most preferably 1-3 vol % benzene. The combined content of benzene and ethylene comprised in the incoming gas is typically in the range 0.5-20 vol %, preferably 2-15 vol %, most preferably 3-7 vol %. All vol % values given here are based on dry volume basis. Even if the optional pre-treatment steps as defined here below would be carried out, the incoming gas typically contains significant amounts of ethylene and monocyclic aromatic compounds such as benzene. A typical application of the incoming gas, particularly in the form of a (biomass and/or waste) gasification product gas, is the manufacture of (bio-)SNG, wherein the gas is subjected to a methanation catalyst to form methane. It is a known problem that ethylene and benzene are coking precursors for methanation catalysts, which is an unwanted side-reaction. Ethylene and benzene as well as any other unsaturated hydrocarbons and monocyclic aromatic compounds thus need to be removed or converted prior to methanation. The process according to the present invention provides an efficient method for such removal and at the same time provides a valuable product in the form of a fraction of monocyclic aromatic compounds.

Possible Pre-Treatment of the Gas

Depending on the exact composition of the gas to be subjected to the process according to the invention, pre-treatment of the gas may be preferred. The incoming gas, especially when originating from a gasification or pyrolysis reactor, is advantageously pre-treated prior to being subjected to step (a). A particularly preferred pre-treatment step is a pre-washing step to remove tar-like components. Such a pre-washing step is described separately as step (c). Further pre-treatment, which may be applied upstream of step (a) and upstream of step (c) in case the latter is included in the process according to the invention, can be used to remove non-gaseous components (e.g. particulate material) from the gas stream, high molecular weight tar-like components and/or polar molecules. Preferably, at least tar-like components of more than 24 ring atoms and particulate material are removed, when present, as such components may be detrimental for effective cleaning of the gas using the process according to the invention.

A pre-cleaning step may be performed, which is especially preferred in case the incoming gas stream contains substantial levels of tar-like components having more than 18 ring atoms, in particular if it contains components of more than 24 ring atoms. Such a pre-cleaning step typically involves contacting the gas stream with another washing or scrubbing liquid prior to being contacted to the washing liquid in step (a) or the pre-washing liquid in step (c). Herein, tar-like components are condensed and collected in the washing liquid, after which they may be separated from the spent washing liquid. The washing liquid to be used in the pre-cleaning step preferably has a high affinity for more complex polycyclic (aromatic) hydrocarbons. Suitable prior scrubbing liquids are aromatic hydrocarbons, for example polyaromatic compounds corresponding to the heavy tar-like compounds present in the gas and/or originate from scrubbing the tar containing gas, comprising polyaromatics having 2-4 rings. Commercially available coal tars or coal tar naphthas (the lighter equivalent of coal tar) mainly consisting of $C_7$-$C_{18}$ hydrocarbons are suitable as washing liquid for pre-cleaning. They will be supplemented during scrubbing with tars extracted from the gas. The pre-cleaning can be performed at a higher temperature than steps (a) and (c), for example between 150 and 900° C., more typically using a liquid inlet temperature of between 150 and 300° C., and a gas inlet temperature between 250° C. and 900° C. Thus, in a preferred embodiment, the gas, prior to step (a) or step (c), is treated with a scrubbing liquid comprising aromatic hydrocarbons, at a temperature of between 150 and 900° C.

In the pre-cleaning step using (poly)aromatic hydrocarbons as washing liquid, the spent washing liquid resulting from the contacting step can be subjected to a separation step using evaporation of the lighter components. These lighter components can be reused as absorption (scrubbing) liquid for the pre-cleaning step. The heavier fraction resulting from the separation step may be discharged. Part of this discharged heavy fraction can be returned to the inlet of a gasification or pyrolysis reactor, in case the incoming gas stream originates from such a reactor, and subjected (again) to gasification or pyrolysis to be converted into lighter components, or it can be used for other purposes such as heating. Further details of the pre-cleaning step using aromatic hydrocarbons are described in WO 2011/037463.

Alternatively or additionally, the gas, e.g. gas issuing from gasification or pyrolysis, may be cleared from dust particles and/or other particulate material (e.g. aerosols) before being subjected to step (a) and optionally step (c), possibly before and/or after the optional pre-cleaning step. Clearing from dust particles may be performed by passing the gas e.g. through an electrostatic filter or an electrostatic precipitator as described in WO 2008/010717. Other methods or devices for clearing dust particles can be used as well, such as an aerosol scavenger as described in WO 2011/099850.

If desired, a further cleaning step can be introduced before or after step (a) and possibly step (c), for example for (further) removing polar compounds such as ammonia and the like, using neutral, acidic or alkaline aqueous scrubbing liquids, or for removing water, e.g. by condensation. Such condensation is advantageously implemented between step (c) and step (a). However, appreciable levels of water, HCl, ammonia, amines and the like are effectively captured by the (pre-)washing liquid, so that additional cleaning steps will often not be necessary. Compounds such as water and ammonia are readily desorbed from the scrubbing liquid, leaving the scrubbing liquid clean and stable. Thus, in one embodiment, the process according to the invention does not comprise a step wherein the gas is contacted with neutral, acidic or alkaline aqueous scrubbing liquids.

The Washing Liquid

The washing liquid that is used in the process according to the invention typically comprises or is an organic solvent, such as aliphatic or aromatic solvents, preferably aliphatic or aromatic hydrocarbons. Typically, an oil is used that is liquid at the conditions at which step (b1) is performed. Such washing liquids are known in the art and any solvent which is known in the art to be suitable in this respect, such as mineral, vegetable or synthetic oils, may be used in the washing liquid. Preferably, the washing liquid comprises at least 75 vol. % of the solvent, more preferably at least 90 vol. % or even at least 95 vol. % of the solvent. It is most preferred that the washing liquid is the solvent as specified herein. In a preferred embodiment, both the washing liquid and the pre-washing liquid contain the same solvent. It is preferable to use a non-volatile oil, and more particularly an oil in which the molecules comprise approximately 15-50 carbon atoms. The term non-volatile is understood as meaning an oil grade which, at a temperature of 70° C., preferably at a temperature of 100° C., releases less than 10 mg of oil per standard cubic metre of cleaned gas. Preferred solvents are selected from hydrocarbon oils (e.g. petroleum oil, coal tar fractions), biomass-derived oils (e.g. vegetable oil, biodiesel, waste cooking oil, wood pyrolysis oil) and silicon oils. In one embodiment, the solvent is a polysiloxane or a mineral aliphatic oil, most preferably a polysiloxane is used. Polysiloxanes have been found especially suitable to be used as washing liquid in steps (b1) and (c1), especially in view of the elevated temperatures used herein and in the subsequent stripping step (b2) and (c2). Mineral and hydrocarbon oils are typically more volatile than the polysiloxane, which hampers stripping especially when steam is used as stripping gas, as steam has a much higher boiling point compared to other suitable stripping gases such as air, nitrogen and/or carbon dioxide.

Thus, in an especially preferred embodiment, the washing liquid comprises or even consists of organic polysiloxanes. Preferably, also the pre-washing liquid comprises or even consists of organic polysiloxanes. The organic polysiloxane to be used comprises an alternating silicon-oxygen chain wherein the silicon is further substituted with organic groups. The organic polysiloxane may also be referred to as poly-diorganyl-siloxane. Preferably the polysiloxane is an aryl polysiloxane, i.e. at least a part of the organic groups are aryl groups, including aralkyl or alkaryl groups. Preferably, the polysiloxane comprises an average of between 0.2 and 1.8 $C_5$-$C_{14}$ aryl groups, more preferably 0.2-1.8 $C_5$-$C_{10}$ aryl groups, per silicon atom. Advantageously, the polysiloxane also comprises alkyl groups, in particular 0.2-1.8 $C_1$-$C_6$ alkyl groups per silicon atom, more in particular 0.2-1.8 $C_1$-$C_4$ alkyl groups per silicon atom. In a preferred embodiment, the polysiloxane comprises an average of between 0.5 and 1.5 $C_5$-$C_{14}$, more preferably 0.5-1.5 $C_5$-$C_{10}$ aryl groups, most preferably 0.5-1.5 $C_6$-$C_8$ aryl groups per silicon atom and/or between 0.5 and 1.5 $C_1$-$C_4$ alkyl groups per silicon atom. The polysiloxane preferentially has a molar weight between 500 and 14,000 g/mol, more preferably between 700 and 7,000 g/mol, most preferably between 1,000 and 5,500 g/mol. The polysiloxane preferably has a narrow size distribution (dispersity), such as a dispersity $M_w/M_w$ in the range of 1-5, preferably 1-2, or even 1-1.2. Such low dispersity enables the use of stripping as efficient clearing of the spent washing liquid. Washing liquids with a broad MW distribution cannot be efficiently stripped and typically require distillation for the contacting of step (b2). Furthermore, relatively small molecules of washing liquid would evaporate during stripping and end up in the loaded stripping gas, hampering the separation of monocyclic aromatic compounds from the stripping gas in step (b3) and consequently polluting the composition of monocyclic aromatic compounds and/or the stripping gas that may be reused in step (b2). The presence of relatively large molecules of washing liquid impart a high viscosity on the washing liquid, which hampers the process and requires greater temperatures for efficient stripping, as such reducing the efficiency of the process. Hence, a narrow size distribution is preferred for the polysiloxane washing liquid. Within the MW ranges defined above, the process according to the invention is performed most optimally.

The polysiloxane can be represented by one of the formulas (I) and (II):

(I)

(ii).

Herein,
each occurrence of $R^1$ and $R^2$ is individually selected from optionally substituted $C_1$-$C_{14}$ hydrocarbyl groups,
n is an integer in the range of 5-100, preferably in the range of 7-40,
n1+n2+n3 equals n, wherein
(n1+n3)/n2 is in the range of 1/9-9/1, preferably in the range of 1/4-4/1, most preferably in the range of 2/3-3/2, and/or
(n2+n3)/n1 is in the range of 1/9-9/1, preferably in the range of 1/3-3/1, most preferably in the range of 2/3-3/2.

Although any hydrocarbyl group known in the art may be suitable, "hydrocarbyl" typically refers to alkyl or aryl. In the context of the present invention, the term "alkyl" includes linear, branched and cyclic alkyl moieties. In the context of the present invention, the term "aryl" includes alkaryl moieties, wherein an alkyl moiety is substituted with an aryl moiety, and aralkyl moieties, wherein an aryl moiety is substituted with an alkyl moiety. The hydrocarbyl moieties may be unsubstituted or substituted, preferably they are unsubstituted. The optional substituents that may be present on the hydrocarbyl groups are preferably selected from hydroxy, alkoxy (e.g. $C_1$-$C_4$ alkoxy), halogen, alkanoyl or acyl (e.g. $C_1$-$C_4$ alkanoyl), carboxy, alkanoyloxy (e.g. $C_1$-$C_4$ alkanoyloxy), alkoxycarbonyl (e.g. $C_1$-$C_4$ alkoxycarbonyl), amino (primary, secondary or tertiary), carbamoyl (e.g. $C_1$-$C_4$ carbamoyl), cyano, nitro. Preferably, the hydrocarbyl is unsubstituted or contains an alkoxy substituent, preferably methoxy.

Preferred polysiloxanes of formulas (I) and (II) are those wherein at least 50% (by number) of the occurrences of $R^1$ are aryl groups, preferably aryl groups having 5-14 carbon atoms, more preferably 5-10 carbon atoms, most preferably of 6-8 carbon atoms, the remaining occurrences of $R^1$ preferably being alkyl groups. Preferably, at least 80% of the occurrences of $R^1$, more preferably at least 95% of the occurrences of $R^1$ are such aryl groups. Aryl groups as used herein include alkylaryl (alkaryl) and arylakyl (aralkyl) groups. Especially preferred aryl groups include phenyl, methylphenyl (tolyl, preferably p-tolyl), methoxyphenyl, benzyl, 2-phenyl-isopropyl, naphthyl and the like. Preferred polysiloxanes of formulas (I) and (II) comprise $C_1$-$C_4$ alkyl groups as $R^2$, most preferably the alkyl groups include methyl and ethyl.

The polysiloxane may be a homopolymer or an alternating, block or random copolymer of dialkyl, alkylaryl and/or diaryl siloxanes. The polysiloxane homopolymer is represented by formula (I), wherein each occurrence of $R^1$ is the same and each occurrence of $R^2$ is the same. The polysiloxane copolymer is represented by formula (II). The polysiloxane can also be a mixture of different poly-dialkyl, polyalkyl-aryl and/or polydiaryl siloxanes. Preferably, the polysiloxane is a poly-methyl-phenyl-siloxane (i.e. formula (I), wherein $R^1$=Ph and $R^2$=Me) or a poly-diphenyl-co-dimethyl-siloxane (i.e. formula (II), wherein $R^1$=Ph, $R^2$=Me and n3=0) or a poly-(methyl-phenyl)-co-dimethyl-siloxane (i.e. formula (II), wherein $R^1$=Ph, $R^2$=Me and n1=0). Preferably the proportion of aryl groups is between 0.5 and 1.5 aryl group per silicon atom. A most preferred polysiloxane is poly(methylphenylsiloxane). Depending on the tar components to be removed and the removal conditions, specific siloxanes, e.g. having specific molecular weight and/or specific organic groups can be prepared and used. Polysiloxanes can be prepared by methods known in the art. Various organic polysiloxanes including poly(methylphenylsiloxane) and poly-diphenyl-co-dimethyl-siloxane are commercially available.

The washing liquid, preferably comprising the polysiloxane as defined herein, is used in both step (b) and preferably in step (c) for contacting with the gas stream. Although the washing liquid used in the two steps may be different, it is preferred that the same polysiloxane is used in both steps. Most preferably, poly(methylphenylsiloxane) is used in both steps.

Step (a)

In step (a), the incoming gas is contacted with a catalyst capable of converting ethylene into monocyclic aromatic compounds, in particular benzene although other monocyclic aromatic compounds such as toluene, xylenes and derivatives (e.g. ethylbenzene) may typically also be formed. Such catalysts are known in the art and any suitable type may be used in step (a). In one embodiment, the catalyst does not convert methane into (monocyclic) aromatic compounds at the operating conditions of step (a), since methane is a desired compound to be present in (bio-)SNG. An especially preferred catalyst comprises a zeolite, which structure may belong to MFI, FAU, TON, MFL, VPI, MEL, AEL, AFI, MWW or MOR families, preferably with a MFI and/or MEL structure, most preferably a MFI structure. In one embodiment, a zeolite having a pentasil structure is used. In a preferred embodiment, the zeolite is ZSM-5 or ZSM-11. Most preferably, a ZSM-5 MFI zeolite is used. The $SiO_2$:$Al_2O_3$ ratio of the zeolite may advantageously vary between 20 and 50. Zeolites such as ZSM-5 are capable of converting ethylene and other unsaturated hydrocarbons into monocyclic aromatic compounds such as benzene via a complex sequence of oligomerization, isomerization, cracking and cyclization reactions that are believed to occur on Brønsted acid sites of the zeolite. The zeolite may be promoted, although satisfactory results have also been obtained with unpromoted ZSM-5. Promoting zeolites is known in the art, and also referred to as loading. This is a well-known procedure which typically involves impregnating or ion-exchanging the zeolite with (an) oxide(s) of the promoting element(s). The zeolite may be promoted with one or more elements selected from Ga, Zn, W, Re, Cu, Mn, Ni, Cr, V, Co, Mo, Ru and Pd. Preferred promoting elements are Ga and/or Zn and/or Mo. Most preferably, the zeolite is promoted with Ga. In one embodiment, the zeolite is not promoted or promoted with Zn and/or Ga and/or Mo, most preferably with Ga. It has been shown that impregnating ZSM-5 with promoters like Ga or Zn which generally promote dehydrogenation reactions, increases the aromatics yield. Also, the use of Ga promotor has been found to increase catalyst stability. Particularly beneficial results have been obtained with Ga promotion. The promoting element(s) may be present in a content of 0.01-10 wt %, preferably 0.1-5 wt %, most preferably 0.2-3 wt %, based on total weight of the zeolite. The promoting element is believed to be bound to the Brønsted acid sites of the zeolite, thus taking the place of bound $H^+$ in the unpromoted zeolite. The molar ratio of promoting elements to remaining bound $H^+$ is preferably in the range of 1/5-5/1, more preferably 1/2-2/1, most preferably 2/3-3/2.

Step (a) is performed under conditions effective for the ethylene to be converted into monocyclic aromatic compounds. Step (a) may thus also be referred to as "converting ethylene (and optionally other unsaturated hydrocarbons) into monocyclic aromatic compounds". Typically, the compounds other than ethylene and the optionally present other unsaturated hydrocarbons are left untouched during step (a). Preferably, step (a) is performed at a temperature in the range of 250-650° C., more preferably 280-600° C., even more preferably 300-550° C., most preferably 450-520° C. Higher temperatures are typically undesirable for process economics and coke formation. Moreover, alkanes including methane may be converted into monocyclic aromatic compounds at such elevated temperatures, which does not hamper the process since it will only increase the yield of monocyclic aromatic compounds. However, the conversion of alkanes is not required in case the purified gas is to be used as feedstock for (bio-)SNG production.

Step (b)

In step (b), the monocyclic aromatic compounds formed in step (a) are isolated from the gas originating from step (a), obtaining a purified gas and a fraction of monocyclic aromatic compounds. In case monocyclic aromatic compounds were already present in the incoming gas, they will be isolated together with the monocyclic aromatic compounds formed in step (a), as a single fraction. Since isolating monocyclic aromatic compounds from a product gas is much easier than isolating ethylene and the obtained fraction of monocyclic aromatic compounds is a valuable product, the present process provides a surprisingly elegant way of purifying product gas from ethylene and monocyclic aromatic compounds and at the same time producing two valuable products, namely a fraction of aromatics besides the main process product (for example, but not limited to, bio-SNG).

The isolating of step (b) may be performed by any means known in the art. In a preferred embodiment, the isolation of step (b) is performed by:

(b1) contacting the gas originating from step (a) with a washing liquid, at a temperature of 15-60° C., to obtain the purified gas and a spent washing liquid;

(b2) contacting the spent washing liquid with a stripping gas comprising steam, to obtain a loaded stripping gas comprising monocyclic aromatic compounds and a stripped washing liquid; and (b3) separating the monocyclic aromatic compounds from the loaded stripping gas obtained in step (b2) to obtain a composition comprising monocyclic aromatic compounds.

Step (b1)

In step (b1) of the process according to the invention, the gas is contacted with a washing liquid at a temperature in the range of 15-60° C., preferably 25-50° C., more preferably 30-40° C., to absorb therein the monocyclic aromatic compounds, such as benzene, toluene and xylene. In one embodiment, step (b1) is performed at a temperature in the range of 31-50° C., preferably 32-48° C., most preferably 33-45° C. Step (b1) may also be referred to as "absorbing". Lower temperatures are undesirable as that would require cost-inefficient active cooling and would render the washing liquid too viscous for efficient absorption of monocyclic aromatic compounds. Higher temperatures are typically used to absorb heavier tar-like components, which are preferably not present in the incoming gas. It was found that increasing the temperature to above 60° C., or even above 50° C., reduced the yield of monocyclic aromatic compounds obtained by the process and afforded a gas that was purified to a lesser extent. All in all, most efficient absorption was observed in the above defined temperature ranges. Preferably, the washing liquid comprises at least 75 vol. % organic polysiloxane, more preferably at least 90 vol. % or even at least 95 vol. % organic polysiloxane. Although minor amounts of other components are allowed, in a preferred embodiment the washing liquid does not contain substantial amounts of water, such as at most 10 vol. % water or even at most 5 vol. % water. The washing liquid may also be referred to as a scrubbing liquid. The pressure may range from below ambient to superatmospheric, typically from 0.5-25 bar, preferably 1-5 bar. Most conveniently, about ambient pressure (about 1 bar) is used.

In step (b1), the monocyclic aromatic compounds are removed from (washed from or scrubbed from) the gas. The contacting of step (b1) affords a purified gas, which is depleted in monocyclic aromatic compounds, and a spent washing liquid, which comprises the monocyclic aromatic compounds. The spent washing liquid comprising monocyclic aromatic compounds is stripped in step (b2). The purified gas is one of the products of the process according to the invention. The purified gas discharged from step (b1) typically contains the following components: $H_2$, CO, $CH_4$, often some small hydrocarbons containing two or three carbon atoms, optionally small sulphur species such as $H_2S$, COS, $CS_2$ and possibly minor amounts of small organic sulphur compounds (e.g. methyl mercaptan), and optionally traces of HCl and ammonia. The purified gas may optionally be further cleaned or converted as explained below.

Step (b2)

After being contacted with the gas, the spent washing liquid containing the monocyclic aromatic compounds is stripped, i.e. the monocyclic aromatic compounds are separated (or removed) from the spent washing liquid, by contacting with a stripping gas. The contacting of step (b2) may also be referred to as "stripping". Stripping is known in the art. As such, the stripped washing liquid may advantageously be used again in step (b1), or even as pre-washing liquid in case step (c) is performed with the same washing liquid. Thus, in a preferred embodiment, the spent washing liquid comprising the monocyclic aromatic compounds is stripped and subsequently returned for a further contact cycle of step (b1). Stripping step (b2) further affords a loaded stripping gas, which comprised the monocyclic aromatic compounds.

Stripping step (b2) preferably involves heating the spent washing liquid and/or lowering the pressure. In one embodiment, stripping is performed at a temperature in the range of 80 to 250° C., preferably 120 to 220° C. Most optimal stripping was observed at a temperature of 160-180° C. Preferably, the temperature is raised to at least 50° C., preferably in the range of 80° C. to 120° C., above the contacting temperature of step (b1). A temperature increase of 20° C. more or less corresponds to a pressure decrease of a factor 2 and a temperature increase of at least 50° C. corresponds to a pressure decrease of a factor of at least 5.6. Thus, at equal temperatures, the stripping is preferably performed at a pressure which is a factor of at least 5.6, more preferably a factor between 16 and 80, below the scrubbing pressure. Also, a temperature increase may be accompanied with a pressure decrease, wherein both the temperature increase and the pressure decrease may be performed to a lower extent. In absolute terms, the stripping can be performed for example at a temperature between 75 and 250° C., in particular between 100 and 220° C., most preferably in the range of 140-180° C. at atmospheric pressure. The inventors surprisingly found that at a temperature above 140° C. and atmospheric pressure stripping of the spent washing liquid could efficiently performed with a stripping gas flow as low as 25% of the initial steam flow (see Example 3, steam flow rate=0.25 m³/h). Such low flow rates are preferred, as the amount of steam needed is reduced and the separation of step (b3) is facilitated. Alternatively, the preferred stripping temperatures are e.g. between 90 and 220° C., preferably between 120 and 190° C. at 0.125 bar. In a preferred embodiment, the temperature is more or less equal within the stripping unit, e.g. in the stripping column or tower. In other words, preferably no temperature gradient is present. The inventors found that a constant temperature throughout the stripping unit ensures that the greatest amount of monocyclic aromatic compounds is separated from the spent washing liquid. As such, the stripped washing liquid can readily be reused in step (b1) or optionally step (c1). The temperature difference within the stripping unit is preferably below 25° C., more preferably below 10° C., or even below 5° C. The absence of a temperature gradient may be accomplished by hearing the spent washing liquid and the stripping gas to about the same temperature before they are introduced in the stripping unit.

During stripping, the spent washing liquid is contacted with a stripping gas. The stripping gas comprises steam, and may contain further gaseous components such as air, carbon dioxide, nitrogen or mixtures thereof. Preferably, the stripping gas comprises at least 50 vol. % steam, more preferably at least 80 vol. % steam, such as at least 90 vol. % or even at least 95 vol. % steam. It is most preferred that the stripping gas is steam, i.e. contains 100 vol. % steam. Pure steam is especially preferred, as it facilitates the separation of the stripping gas, the monocyclic aromatic compounds and possibly any remaining permanent gases in step (b3). Thus, in an especially preferred embodiment, the loaded stripping gas is subjected to separation step (b3).

The skilled person is capable of adjusting the flow rate of the stripping gas in step (b3) to obtain efficient stripping. The efficacy of the stripping may for example depend on the temperature at which step (b2) is performed. For example, a reduced temperature is preferably accompanied with an increased flow rate, and vice versa. In a continuous process, the flow rate is conveniently set such that the amount of stripped washing liquid per unit of time more or less equals the required amount of the washing liquid to efficiently scrub the incoming gas. The flow rate wherein step (b2) is performed is preferably 0.1-5 times greater, more preferably 0.5-2 times greater, than the flow rate at which step (b1) is performed. Using such flow rates, a sufficient amount of washing liquid is stripped in step (b2) for efficient washing of the gas in step (b1), such that step (b1) may be performed continuously. Efficient continuous stripping was observed using flow rates of 0.25, 0.5 and 1 m³/h steam. Preferably, a flow rate or 0.02-5 m³/h steam, more preferably 0.1-0.5 m³/h steam, most preferably 0.2-0.4 m³/h steam is used during step (b2). These steam flow rates are advantageously combined with a flow rate of gas in step (b1) of 1-50 L/min, more preferably 5-40 L/min, most preferably 10-25 L/min. Low flow rates are preferred, as the amount of steam needed is reduced and the separation of step (b3) is facilitated.

Step (b3)

Advantageously, the loaded stripping gas is subjected to separation step (b3). Herein, the monocyclic aromatic compounds are separated from the stripping gas. Separation step (b3) provides the stripping gas and an oily fraction of monocyclic aromatic compounds. The stripping gas is preferably reused in another cycle of step (b2). As the stripping gas contains steam, step (b3) is effectively performed by condensation, providing an immiscible liquid composition comprising water and monocyclic aromatic compounds. Collection of this composition in a vessel allows for liquid-liquid separation thereof, as known in the art. Such separation is conveniently based on refractive index. In the context of the present invention, the term "stripping gas" is used for the gas used to strip the washing liquid, also after condensation thereof such as in step (b3). Stripping gas may thus refer to a liquid such as water.

Condensation is preferably accomplished by lowering the temperature of the stripping gas comprising the light tar-like components to below the dew point of water. Conveniently, the temperature is reduced to 4-40° C., preferably to 5-30° C., preferably at ambient pressure. Ambient temperature (typically 15-25° C.) may conveniently be used, as no active cooling (to below ambient temperature) is required. However, using further reduced temperatures such as 4-15° C., preferably 5-8° C. may be also convenient, as the amount of gaseous water and tar-like components is further reduced. At such reduced temperature, both the water and the monocyclic aromatic are typically predominantly in the liquid phase (although some remaining gaseous molecules may be present), but in view of their immiscible character, they form a two-layer system which is readily separated based on refractive index. Cooling to below 4° C. is not suitable, as the mixture of monocyclic aromatic compounds, typically containing benzene as major component, solidifies below 4° C., which hampers separation. The melting temperature of the mixture of monocyclic aromatic compounds is typically slightly below that of benzene ($T_m=5.5°$ C.) as the presence of other (monocyclic aromatic) compounds reduces the melting temperature compared to pure benzene. Typically, both the aqueous fraction and the organic fraction containing the monocyclic aromatic compounds are drained separately.

According to a preferred embodiment of step (b3), condensation is performed by two consecutive steps. First, the loaded stripping gas is subjected to condensation at a temperature of 15-40° C., preferably 25-35° C., more preferably at ambient temperature. Employing such temperatures reduces the operating costs associated with cooling the bulk of loaded stripping gas that is fed to module (b3), while at the same time enables condensation of the majority of the stripping gas and the monocyclic aromatic compounds comprised therein. The condensed liquids are subjected to liquid-liquid separation as described above, while the remainder of the loaded stripping gas, i.e. which is not condensed, is subjected to a second condensation step at a temperature of 4-10° C., preferably 4-5° C. At such temperatures, the remaining components of the loaded stripping gas are readily condensed, except for the permanent gases dissolved in the loaded stripping gas. As such, the operating costs for cooling are kept as low as possible, as only a minor part of the loaded stripping gas is subjected to the second condensation step, while efficient collection of substantially all of the monocyclic aromatic compounds that are stripped from the washing liquid is readily accomplished. Herein, two immiscible liquid phases are obtained, which may be combined before or after separation into condensed stripping gas and monocyclic aromatic compounds. Preferably, the immiscible compositions are combined prior to separation thereof, such that only a single separation step is needed. Most conveniently, the immiscible composition obtained in the second condenser, which is typically colder and of less volume, is led to the immiscible composition of the first condenser, where separation takes place. An alternative approach is to combine both aqueous layers to form a single aqueous layer, which after draining and vaporization may be reused as stripping gas, while both organic layers are drained separately and optionally combined afterwards.

The drained aqueous fraction(s) consist(s) essentially of water and may be reused as stripping gas, after heating to above the dew point of water. The drained organic fraction(s) consist(s) essentially of the monocyclic aromatic compounds, and typically comprises at least 75 wt. % or even at least 90 wt. % of the combined content of benzene, toluene and xylene (BTX), based on total weight of the organic fraction. Typically, the majority of the BTX fraction is benzene, such as at least 80 wt % or even at least 90 wt %, although the composition might vary depending on the operating conditions of step (a) The fraction of monocyclic aromatic compounds typically contains benzene, toluene, xylene, and possibly traces of other aromatic compounds such as styrene, ethylbenzene, cresol, naphthalene and thiophene. Herein, "traces" means less than 1 wt. %, based on total weight of the organic fraction. The content of polycyclic aromatic compounds (containing two or more rings) is typically below 5 wt %, preferably below 2 wt % or even below 1 wt %. As this organic fraction or "BTX fraction" is a valuable product of the process of the invention, it is advantageously separated from the stripping gas in step (b3).

In addition to a liquid aqueous phase (the stripping gas) and a liquid organic phase, a small percentage, typically less than 2 vol. %, of the loaded stripping gas that is obtained in step (b2) is formed by permanent gases (i.e. compounds that remain gaseous even after reduction of the temperature below the dew point of water). During contacting step (b1), minor amounts of these permanent gases (e.g. $CH_4$, CO, $CO_2$) may be absorbed by the washing liquid and led to step (b2) where they are stripped together with the monocyclic aromatic compounds. Typically, the permanent gas mainly contains $CO_2$, as that has the highest affinity for the washing liquid. These gaseous compounds are preferably recombined with the gas before this is subjected to step (b1). As such, any further remaining monocyclic aromatic compounds in the gas phase are removed from this remaining gas stream in a further contacting step (b1). As such, the maximal amount of valuable components are extracted from the incoming gas stream and the yield of the purified energy gas that is obtainable by the process according to the invention is maximized. At the same time contamination of the stripping gas is prevented, which may thus be used longer (i.e. more cycles) before the need of cleaning or discarding and replacing thereof.

The major advantage of using steam as stripping gas is that separation in step (b3) is easily and efficiently accomplished, e.g. as described above by condensation of the stripping gas. In case a different stripping gas, such as air, nitrogen or carbon dioxide, would be used, this stripping gas would not be condensed in step (b3) and thus classifies as a permanent gas. Separation between the stripping gas and the remaining gaseous compounds originating from the incoming gas stream (i.e. permanent gases) would not be feasible and valuable compounds would be lost in the cleared stripping gas. A further advantage of the use of steam as stripping gas in step (b2) and the separation of step (b3) is that any washing liquid that may be led along with the loaded stripping gas from step (b2) to step (b3) is not lost (e.g. in a permanent gas stream or irreversibly deposited somewhere in the system), but may be recovered in separation step (b3). The inventors found that traces of washing liquid accumulate as a third layer on the bottom of the collection vessel. Emptying this vessel for collection of the monocyclic aromatic compounds and the condensed stripping gas allows for easy collection of these traces of washing liquid, which are thus not lost but may instead be reused as washing liquid.

Removal of Tar-Like Components (Pre-Washing Step (c))

Depending on the origin and composition of the (optionally pre-treated) incoming gas, a pre-washing step (c) may be advantageously included in the process according to the invention. For example, an energy gas originating from gasification or pyrolysis of biomass, coal, waste, or a combination thereof, typically contains substantial amounts of tar-like components, such as aromatic compounds having a boiling point above 300° C. (when determined at ambient pressure). Such tar-like components are preferably removed from the gas prior to it being subjected to step (a). In such instances, it is preferred that the process according to the invention comprises a step (c) wherein tar-like components are removed by pre-washing. Pre-washing step (c) typically involves a step (c1) wherein the gas is contacted with a pre-washing liquid at a temperature of 60-150° C., to obtain a detarred gas which is fed to step (a) and a spent pre-washing liquid; and a step (c2) wherein the spent pre-washing liquid is contacted with a stripping gas, to obtain a loaded stripping gas and a stripped pre-washing liquid. To distinguish the stripping gas used in step (b2) from the stripping gas used in step (c2), the latter is also referred to as "tar stripping gas".

Step (c) may be performed after (i.e. downstream of) the possible pre-treatment of the incoming gas, as described above. Thus, in a preferred embodiment, the optionally pre-treated gas is subjected to removal of tar-like components in step (c) prior to being subjected to step (a). It is especially preferred that the incoming gas is pre-treated as described above, subjected to step (c) and subsequently subjected to step (b1), in order to obtain the purified gas.

Step (c1)

In step (c1), the optionally pre-treated gas is contacted with a pre-washing liquid at elevated temperatures, such as a temperature between 60 and 150° C., preferably between 65 and 120° C., more preferably between 70 and 100° C., to absorb therein the tar-like components. The above contacting (scrubbing) temperatures apply at atmospheric or slightly superatmospheric conditions. When using higher pressures, the temperatures will typically be higher so as to have comparable vapour pressures of the various components. As a rough rule of thumb, a doubling of the pressure corresponds to a higher temperature of about 20° C. Thus, an absorption step performed at 80° C. and 1 bar is roughly equivalent to a step performed at 100° C. and 2 bar, or at 145° C. at 10 bar. The pressure may thus range from below ambient to superatmospheric, typically from 0.5-50 bar, preferably 1-15 bar. Most conveniently, about ambient pressure (about 1 bar) is used.

The pre-washing liquid preferably comprises at least one selected from hydrocarbon oil, mineral oil and the polysiloxane as defined above, more preferably the pre-washing liquid comprises the polysiloxane. Preferably, the pre-washing liquid comprises at least 75 vol. % organic polysiloxane, more preferably at least 90 vol. % or even at least 95 vol. % organic polysiloxane. It is most preferred that the pre-washing liquid is the organic polysiloxane.

In step (c1), tar-like components are removed from (washed from or scrubbed from) the incoming gas. The contacting of step (c1) affords a detarred gas (i.e. a gas depleted in tar-like components) and a spent pre-washing liquid which comprised the tar-like components. The detarred gas depleted is led to step (a), while the spent pre-washing liquid is stripped in step (c2). Prior to being subjected to step (a), the detarred gas originating from step (c1) may be led through a cooler and/or condenser.

Step (c2)

After being contacted with the gas, the spent pre-washing liquid is stripped, i.e. the tar-like components are separated (or removed) from the pre-washing liquid. Stripping is known in the art. As such, the stripped pre-washing liquid may advantageously be used again as pre-washing liquid in step (c1), or even as washing liquid in step (b1) in case the same washing liquid is used in both the pre-washing liquid and the washing liquid. Thus, in a preferred embodiment, the spent pre-washing liquid is stripped and subsequently returned for a further contact cycle of step (c1). Stripping step (c2) further affords a loaded tar stripping gas which comprised the tar-like components.

Stripping step (c2) preferably involves heating the spent pre-washing liquid and/or lowering the pressure. Preferably, the temperature is raised to at least 50° C., preferably in the range of 80° C. to 120° C. above the contacting temperature of step (c1). A temperature increase of 20° C. more or less corresponds to a pressure decrease of a factor 2 and a temperature increase of at least 50° C. corresponds to a pressure decrease of a factor of at least 5.6. Thus, at equal temperatures, the stripping is preferably performed at a pressure which is a factor of at least 5.6, more preferably a factor between 16 and 80, below the scrubbing pressure. Also, a temperature increase may be accompanied with a pressure decrease, wherein both the temperature increase and the pressure decrease may be performed to a lower extent. In absolute terms, the stripping can be performed for example at a temperature between 100 and 250° C., in particular between 120 and 220° C., most preferably in the range of 150-180° C. at atmospheric pressure. Alternatively, the preferred stripping temperatures are e.g. between 90 and 220° C., preferably between 120 and 190° C. at 0.125 bar.

During stripping, the spent pre-washing liquid is contacted with a tar stripping gas. The tar stripping gas preferably comprises air, carbon dioxide, nitrogen, steam or mixtures thereof, more preferably the tar stripping gas is nitrogen or air, most preferably the tar stripping gas is nitrogen. The use of nitrogen or air is especially preferred in case the process according to the invention is implemented in a gasification or pyrolysis process. The loaded tar stripping gas, which comprises the tar-like components, is advantageously recycled to the gasification or pyrolysis reactor, either as feedstock to convert the tar-like components into valuable compounds for e.g. SNG or as fuel for heating the reactor. In such an environment, the presence of steam is undesirable. Alternatively, the tar-like components are separated from the tar stripping gas. In case, the tar-like components are separated from the loaded tar stripping gas, a cleared tar stripping gas and a fraction comprising tar-like components is obtained. The cleared tar stripping gas is preferably reused in another cycle of step (c2). Tar separation may be performed in similar fashion as the separation of step (b3), such as by condensation conveniently caused by a temperature decrease.

Post-Treatment

The purified gas (the gas depleted in heavy and light tar-like components), as obtained in step (b) of the process according to the invention, may be further treated, for example by sulphur removal and/or reforming. These two steps are commonly applied in the process of preparing (bio-)SNG to an energy gas obtained from gasification or pyrolysis. Herein, sulphur removal is typically accomplished by hydrodesulphurisation (HDS) and/or solid adsorption (e.g. ZnO). During HDS, sulphur containing compounds such as thiols, thioethers and thiophenes are converted to $H_2S$, which is subsequently removed from the gas stream. Methods and means for HDS are known in the art and include catalytic or biological hydrogenation and subsequent removal of $H_2S$, e.g. by alkaline absorption or limited biological oxidation to produce elemental sulphur. However, in view of the removal of aromatic compounds according to the process according to the invention, both sulphur removal and reforming may not be required at all or needed to a lesser extent, compared to prior art processes. As such, sulphur removal may be accomplished efficiently by adsorption, e.g. to activated carbon, ZnO or other adsorption media, which is significantly more efficient in terms of costs and energy than HDS.

The inventors found that the gas after step (b) is substantially free from thiophene, such that sulphur removal may not be needed, or only for the removal of sulphur-containing organic compounds smaller than thiophene (e.g. methyl or ethyl mercaptan, dimethyl sulphide), if present at all. HDS may be performed as sulphur removal step, for the removal of sulphur containing compounds such as methyl or ethyl mercaptan and dimethyl sulphide. As removal of thiophene is not needed, and thiophene is among the most challenging compounds to be removed by HDS, the HDS post treatment of the purified gas may be more flexible in terms of temperatures employed and type of catalyst used, compared to prior art processes. Depending on the composition of the incoming gas stream, sulphur capture may alternatively be performed by contacting the purified gas with activated carbon or may not even be needed altogether.

The purified gas may be subjected to (steam) reforming, wherein the remaining hydrocarbon compounds in the purified gas, typically containing 2 to 4 carbon atoms, are converted into $H_2$ and CO and/or $CO_2$ (syngas), and subsequently into methane (methanation), to obtain (bio-)SNG. Steam reforming is performed in the presence of steam and a metal-based catalyst, often nickel-based. Reforming is typically performed after sulphur removal, if sulphur removal is performed at all, as sulphur will poison the reforming catalyst. Since tar-like components, including light tars such as benzene, are effectively removed from the gas stream prior to reforming, reforming of the purified gas is much easier compared to reforming in prior art processes for the production of (bio-)SNG. Therein, compounds like benzene need to be converted into syngas, which places a greater burden on the reforming step in terms of energy and catalyst needed. Such gasification for the preparation of (bio-)SNG is for example known e.g. from WO 2007/061301 and WO 2010/120171. Removal of benzene is also needed when the gas originating from biomass and/or coal gasification or pyrolysis is used as fuel in e.g. a gas engine, as such engines typically do not combust benzene (completely) which would lead to too much emission of benzene into the environment. Conventionally, benzene (as well as other monocyclic aromatics) is removed by steam reforming, which may be replaced by the process according to the invention, which effectively removes and recovers benzene from gas streams during step (b).

As alternative to reforming, the remaining hydrocarbon compounds containing two or more carbon atoms may be separated from the purified gas, after which mainly $H_2$, CO, $CO_2$ and $CH_4$ remain. The remaining purified gas stream may be subjected to methanation to obtain (bio-)SNG. Such separation of hydrocarbons is known in the art and typically involves the use of a deethaniser, depropaniser, debutaniser, $C_3$-splitters, and the like.

System

The invention also concerns an apparatus or system specifically designed to implement the process according to the invention. The system according to the invention is a modular system, in which at least two, preferably at least three, four, five or even six modules (or units) are in fluid connection with each other. Herein, each module may be a separate unit or two or more modules may be integrated as a single unit. Preferably, each module is a separate unit and is distinguishable as such in the system. The modular system for performing the process according to the invention is suitably incorporated into a (coal, biomass or waste) gasification plant or a pyrolysis plant. The system according to the invention is described with reference to FIG. 1.

The modular system according to the invention comprises:

(a) an ethylene conversion module for converting ethylene into monocyclic aromatic compounds, comprising a gas inlet (a1) for receiving the incoming gas, a catalyst (a2) capable of converting ethylene into monocyclic aromatic compounds and a gas outlet (a3) for discharging a gas enriched in monocyclic aromatic compounds;

(b1) an absorbing unit comprising a gas inlet (b11) for receiving the gas enriched in monocyclic aromatic compounds, a liquid inlet (b12) for receiving a washing liquid, a gas outlet (b14) for discharging a purified gas and a liquid outlet (b15) for discharging a spent washing liquid;

(b2) a stripping unit, comprising a liquid inlet (b21) for receiving the spent washing liquid, a gas inlet (b22) for receiving a stripping gas, a gas outlet (b23) for discharging a loaded stripping gas and a liquid outlet (b24) for discharging a stripped washing liquid;

(b3) preferably a separating module, comprising a gas inlet (b31) for receiving the loaded stripping gas, means (b32) for separating the monocyclic aromatic compounds from the stripping gas, an outlet (b33) for discharging a cleared stripping gas, and an outlet (b34) for discharging the monocyclic aromatic compounds;

(c1) preferably a pre-washing unit comprising a gas inlet (c11) for receiving a gas comprising tar-like components and monocyclic aromatic compounds, a liquid inlet (c12) for receiving a pre-washing liquid, a gas outlet (c14) for discharging a detarred gas and a liquid outlet (c15) for discharging a spent pre-washing liquid; and (c2) preferably a tar stripping unit, comprising a liquid inlet (c21) for receiving the spent pre-washing liquid, a gas inlet (c22) for receiving a tar stripping gas, a gas outlet (c23) for discharging loaded tar stripping gas and a liquid outlet (c24) for discharging a stripped pre-washing liquid.

In the system according to the invention, the different modules are interconnected, i.e. the outlet of one module is in fluid connection with the inlet of another module, preferably by means of a conduit. As such, constant flow of (liquid or gas) streams through the system is enabled. Thus, outlet (a3) is in fluid connection with inlet (b11), outlet (b15) is in fluid connection with inlet (b21) and preferably outlet (b24) is in fluid connection with inlet (b12). In case module (b3) is present, outlet (b23) is in fluid connection with inlet (b31) and outlet (b33) is preferably in fluid connection with inlet (b22). In case module (c1) is present, outlet (c14) is in fluid connection with inlet (a1). In case module (c2) is present, outlet (c15) is in fluid connection with inlet (c21) and preferably outlet (c24) is in fluid connection with inlet (c12).

The system according to the invention comprises at least modules (a), (b1) and (b2), and preferably further comprises at least module (b3), most preferably the system according to the invention comprises modules (a), (b1), (b2), (b3), (c1) and (c2).

Ethylene Conversion Module (a)

The system comprises an ethylene conversion module (a), wherein ethylene can be converted into monocyclic aromatic compounds. Module (a) may also be referred to as a reactor or even bed reactor. The gas received by unit (b) may originate from pre-washing unit (c1) and is thus optionally detarred. Module (a) comprises a gas inlet (a1) in one part, preferably the top part, of the module for receiving the incoming gas, and a gas outlet (a2) in another part, preferably the bottom part, of the module for discharging the gas enriched in monocyclic aromatic compounds. Herein, "enriched in monocyclic aromatic compounds" indicates that the concentration (based on total dry volume) of monocyclic aromatic compounds is greater in the gas that is discharged from module (a), compared to the concentration in the gas that is introduced into module (a). Module (a) further comprises a catalyst (a2) capable of converting ethylene into monocyclic aromatic compound. The catalyst is further defined above. Module (a) is configured such that the incoming gas can be contacted with the catalyst. Typically, module (a) is designed such that the incoming gas from inlet (a1) is led through or over a catalyst bed towards outlet (a3).

Module (a) is preferably designed to operate at a temperature in the range of 250-650° C., more preferably 280-600° C., even more preferably 300-550° C., most preferably 450-520° C.

In a preferred embodiment, the system according to the invention comprises a module (a) comprising more than one, preferably at least two, most preferably two or three reactors. Each of the reactors is designed as described above. In case two or more reactors are used, the system is capable of using the first reactor for the contacting of step (a) of the process according to the invention, while the second reactor is being regenerated. Regeneration can be typically performed in the presence of a gas, such as $N_2$, air, or mixtures thereof, preferably at a temperature of 300-700° C.

Absorbing Unit (b1)

The system comprises an absorbing unit (b1) for absorbing the monocyclic aromatic compounds from the gas containing monocyclic aromatic compounds. The gas received by unit (b1) originates from ethylene conversion module (a). Unit (b1) comprises a gas inlet (b11) in one part, preferably the bottom part, of the unit for receiving the gas to be purified from monocyclic aromatic compounds, and a liquid inlet (b12) in another part, preferably the top part, of the unit for receiving the washing liquid. Thus, inlets (b11) and (b12) are preferably located in opposite parts of the unit (b1). In case unit (c1) is present, inlet (b11) is in fluid connection with outlet (c14). The connectivity between outlet (a3) and inlet (b11) may contain a condenser (b18), a pump (b16), a safety filter (b17) and means (b13) for heating or cooling, typically a heat exchanger. Contact between the gas flowing in one direction, typically up-flowing gas, and the liquid flowing in another direction, preferably opposite direction (i.e. counter-current), typically down-flowing liquid, can be enhanced by conventional means such as by spraying, using a packed column or a plate column. Although co-current washing or scrubbing is feasible, a counter-current mode, preferably using a packed column, is preferred. Purified gas can leave unit (b1) through gas outlet (b14), which is preferably located opposite to gas inlet (b11), most preferably at the top part of unit (b1). Spent washing liquid in which the monocyclic aromatic compounds are absorbed, is collected, typically at the bottom, and discharged through liquid outlet (b15).

The absorbing unit (b1) may further comprise a condenser (b18) for removing water and traces of ammonia and HCl if present in the incoming gas. If present, condenser (b18) is located upstream of inlet (b11). Condenser (b18) preferably operates at a temperature of 2-15° C., most preferably 3-7° C. Safety filter (b17), if present, may for example be an aerosol filter or an electrostatic precipitator. The absorbing unit (b1) may further comprise means (b13) for heating and/or cooling, typically for cooling the gas, in particular the mixture of gas and washing liquid during contacting, such that absorption can be operated at temperatures in the range of 15 to 60° C. Means (b13) may be located upstream of inlet (b11), i.e. in the connectivity between outlet (c14) and inlet (b11), and downstream of condenser (b18), if present, such that the gas to be purified from monocyclic aromatic compounds is brought to the desired temperature prior to introduction in unit (b1). Means (b13) typically take the form of a heater or heat exchanger as known in the art. It is preferred that unit (b1) is designed to operate at atmospheric or slightly superatmospheric pressures.

Stripping unit (b2)

The system preferably comprises a stripping unit (b2), wherein the monocyclic aromatic compounds are desorbed from the washing liquid by a stripping gas. The stripping unit can be a tray tower, packed column, bubble column, spray tower or the like. The stripping gas can be co-currently or, preferably, counter-currently contacted with the spent washing liquid. Unit (b2) comprises a liquid inlet (b21) for receiving the spent washing liquid originating from unit (b1). Inlet (b21) is in fluid connection with outlet (b15). The connectivity between outlet (b15) and inlet (b21) may contain a pump (b25), a safety filter (b26) and a heater (b27). Unit (b2) further comprises a gas inlet (b22) for receiving a stripping gas. In a preferred configuration of unit (b2), inlets (b21) and (b22) are located at opposite parts of the unit (b2), preferably liquid inlet (b21) is located in the top part of the unit (b2) and gas inlet (b22) is located in the bottom part of unit (b2). The loaded stripping gas, which comprises the monocyclic aromatic compounds, may be discharged via gas outlet (b23). Unit (b2) further comprises a liquid outlet (b24) for discharging a stripped washing liquid, which is preferably returned to absorption unit (b1) through fluid connection between outlet (b24) and inlet (b12), optionally through a pump (b28) and a cooler (b29), to enable reuse of the washing liquid in unit (b1). Heater (b27) and cooler (b29) are advantageously in heat exchanging communication. Heater (b27) is preferably capable of raising the temperature of the spent washing liquid at least 50° C., preferably in the range of 80° C. to 120° C., with respect to the temperature in unit (b1). Instead of or in addition to heater (b27) and cooler (b29), depressurising and pressurising devices can be inserted.

Stripping unit (b2) is preferably designed to operate at a temperature between 70 and 120° C. above the temperature of the absorption column, more preferably about 100° C. above the temperature of the absorption column. Stripper (b2) preferably is capable of operating at a temperature in the range of 120 to 250° C. Heater (b27) is preferably capable of raising the temperature of the spent washing liquid to such a temperature. In a preferred embodiment, unit (b2) is designed to operate at reduced pressure compared to unit (b1).

Separation Module (b3)

The loaded stripping gas issuing from stripping unit (b2) through outlet (b23) is advantageously led to separation module (b3). Separation module (b3) comprises an inlet (b31) for receiving the loaded stripping gas from module (b2). Inlet (b31) is in fluid connection with outlet (b23). The connectivity between outlet (b23) and inlet (b31) may contain a pump (b38). The loaded stripping gas is received to means (b32) for separating the monocyclic aromatic compounds from the loaded stripping gas. In a preferred embodiment, means (b32) includes a condenser, wherein the loaded stripping gas is cooled and at least the monocyclic aromatic components and the steam of the stripping gas are capable of condensing. Condenser (b32) preferably is a cooler optionally in combination with a pressurising device, and preferably is capable of operating at a temperature of 4-40° C., preferably 5-30° C. Preferably, means (b32) in the form of a condenser is capable of condensing both the monocyclic aromatic compounds and the steam comprised in the stripping gas. The skilled person understands how to design condenser (b32) in order to condense the monocyclic aromatic compounds and the stripping gas, depending on the nature of the stripping gas. According to this embodiment, it is preferred that the stripping gas is steam, such that condensation of substantially all of the stripping gas in condenser (b32) is easily accomplished. Module (b3) further comprises an outlet (b33) for discharging the cleared, typically condensed stripping gas, and an outlet (b34) for discharging the monocyclic aromatic components. Outlet (b33) is preferably in fluid connection with inlet (b22), optionally via a mass flow controller and a heater (b37) that is capable of vaporizing the stripping gas if discharged in condensed form from outlet (b33), to enable reuse of the stripping gas.

Module (b3) preferably further comprises a collection vessel (b35), wherein the condensed liquids emerging from condenser (b32) are collected. The collection vessel (b35) is equipped with a liquid outlet (b34) for discharging monocyclic aromatic compounds and a liquid outlet (b33) for discharging the condensed stripping gas. Vessel (b35) is advantageously equipped with means for liquid-liquid separation, as known in the art. Such separation is capable of separating a two-layer liquid system comprising an aqueous layer of condensed stripping gas and an organic layer of condensed monocyclic aromatic compounds typically including benzene, toluene and xylene. Such separation is conveniently based on refractive index. Herein, outlet (b33) is preferably in fluid connection with inlet (b22) of stripping unit (b2), preferably via a heater (b37) that is capable of vaporizing the condensed stripping gas to enable reuse of the stripping gas in unit (b2).

A preferred configuration of module (b3) is depicted in FIG. 1B. Herein, means (b32) contains two condensers (b32a) and (b32b), both equipped with a collection vessel (b35a) and (b35b). Loaded stripping gas entering module (b3) via inlet (b31) is led to a first condenser (b32a), which is capable of operating at a temperature of 15-35° C., preferably at ambient temperature. Employing such temperatures reduces the operating costs associated with cooling the bulk of loaded stripping gas that is fed to module (b3), while at the same time enables condensation of the majority of the monocyclic aromatic compounds comprised in the loaded stripping gas. The condensed liquids emerging from condenser (b32a) are collected in collection vessel (b35a), which is advantageously equipped with means for liquid-liquid separation. The remainder of the loaded stripping gas, i.e. which is not condensed in the first condenser (b32a), is led to a second condenser (b32b), which is capable of operating at a temperature of 4-10° C., preferably 4-5° C. At such operation temperatures, the remaining components of the loaded stripping gas are capable of condensing, except for the permanent gases dissolved in the loaded stripping gas. As only a minor part of the loaded stripping gas is fed to condenser (b32b), the operating costs for cooling are kept as low as possible, while efficient collection of substantially all of the monocyclic aromatic compounds that are stripped from the washing liquid is readily accomplished. The permanent gases are discharged from module (b3) via outlet (b36), while the condensate is collected in collection vessel (b35b), which is advantageously equipped with means for liquid-liquid separation. The immiscible compositions that are collected in vessels (b35a) and (b35b) may be combined, preferably in one of the collection vessels, which is equipped with means for liquid-liquid separation, while the other collection vessel contains a liquid outlet for discharging the immiscible composition the prior collection vessel. The collection vessel equipped with means for liquid-liquid separation then contains a liquid inlet for receiving the immiscible composition from the other collection vessel, and a liquid outlet for discharging condensed monocyclic aromatic compounds and a liquid outlet for discharging the condensed stripping gas. Conveniently, collection vessel (b35a) is equipped with means for liquid-liquid separation, and contains a liquid inlet (b39) for receiving the immiscible composition from the collection vessel, and a liquid outlet (b34a) for discharging condensed monocyclic aromatic compounds and a liquid outlet (b33a) for discharging the condensed stripping gas. In this embodiment, collection vessel (b35b) contains a liquid outlet (b33b) for discharging an immiscible composition of condensed monocyclic aromatic compounds and condensed stripping gas. Herein, outlet (b33b) is in fluid connection with inlet (b39). In an alternative embodiment, collection vessel (b35b) further comprises a liquid outlet (b34b) for discharging condensed monocyclic aromatic compounds while liquid outlet (b33b) is used for discharging condensed stripping gas to collection vessel (b35a). As such, all condensed stripping gas is collected in a single collection vessel, from which it is discharged and preferentially returned to module (b2). Thus, outlet (b33a) is preferably in fluid connection with inlet (b22) of stripping unit (b2), preferably via a mass flow controller and a heater (b37) that is capable of vaporizing the condensed stripping gas to enable reuse of the stripping gas in unit (b2). A single fraction of monocyclic aromatic compounds is discharged via outlet (b34a), or two fractions of monocyclic aromatic compounds are discharged via outlets (b34a) and (b34b) respectively, which may or may not be combined afterwards.

Absorbing Unit (c)

The system according to the invention preferably comprises a second combination of an absorbing unit and a stripping unit. In this embodiment, the system comprises a pre-washing unit (c1) and a tar stripping unit (c2).

In unit (c1), the incoming gas is detarred prior to being led to unit (a) for conversion of ethylene into monocyclic aromatic compounds. Unit (c1) comprises a gas inlet (c11) in one part, preferably the bottom part, of the unit for receiving the gas to be purified, and a liquid inlet (c12) in another part, preferably the top part, of the unit for receiving the pre-washing liquid. Thus, inlets (c11) and (c12) are preferably located in opposite parts of the unit (c1). Contact between the gas flowing in one direction, typically up-flowing gas, and the liquid flowing in another, preferably opposite, direction, typically down-flowing liquid, can be enhanced by conventional means such as by spraying, using a packed column or a plate column. Although co-current washing or scrubbing is feasible, a counter-current mode, preferably using a packed column, is preferred. Detarred gas can leave unit (c1) through gas outlet (c14), which is preferably located opposite to gas inlet (c11), most preferably at the top. Spent pre-washing liquid, in which the tar-like components are absorbed, is typically collected at the bottom and discharged through liquid outlet (c15). Gas outlet (c14) is in fluid connection with inlet (a1) of unit (a). The fluid connection between outlet (c14) and inlet (a1) may advantageously contain a cooler (e.g. condenser (b18)) and/or an ammonia removal unit (d3).

The absorbing unit (c1) may further comprise means for heating the gas and/or the washing liquid, in particular the mixture of gas and washing liquid during contacting, such that absorption can be operated at temperatures in the range of 60 to 150° C. Such means (c13) may also be located prior to inlet (c11), such that the gas to be cleaned is heated prior to introduction in unit (c1). Means (c13) typically take the form of a heater as known in the art. However, means for heating the gas are typically not required, as the gas entering unit (c1) is typically of about the desired temperature and the temperature within unit (c1) is mainly governed by the temperature of the washing liquid. Typically, the washing liquid, when discharged from a module (c2) is heated to the desired temperature. It is preferred that unit (c1) is designed to operate at atmospheric or slightly superatmospheric pressures.

Tar Stripping Unit (c2)

The system according to the invention preferably comprises a stripping unit (c2) for stripping the spent pre-washing liquid. Stripping unit (c2) is also referred to as a tar stripping unit. Herein, the tar-like components are desorbed from the pre-washing liquid by a stripping gas. The stripping unit can be a tray tower, packed column, bubble column, spray tower or the like. The stripping gas can be co-currently or, preferably, counter-currently contacted with the spent washing liquid. Unit (c2) comprises a liquid inlet (c21) for receiving the spent pre-washing liquid originating from unit (c1). Inlet (c21) is in fluid connection with outlet (c15). The connectivity between outlet (c15) and inlet (c21) may contain a pump (c25), a safety filter (c26) and a heater (c27). Unit (c2) further comprises a gas inlet (c22) for receiving a stripping gas, also referred to as the tar stripping gas. In a preferred configuration of unit (c2), inlets (c21) and (c22) are located at opposite parts of the unit (c2), preferably liquid inlet (c21) is located in the top part of the unit (c2) and gas inlet (c22) is located in the bottom part of unit (c2). The loaded tar stripping gas, containing the tar-like components, may be discharged via gas outlet (c23). Unit (c2) further comprises a liquid outlet (c24) for discharging the cleared pre-washing liquid, which is preferably returned to absorption unit (c1) through fluid connection between outlet (c24) and inlet (c12), optionally through a pump (c28) and a cooler (c29), to enable reuse of the pre-washing liquid in unit (c1). Heater (c27) and cooler (c29) are advantageously in heat exchanging communication. Instead of or in addition to heater (c27) and cooler (c29), depressurising and pressurising devices can be inserted.

Tar stripping unit (c2) is preferably designed to operate at a temperature between 70 and 120° C. above the temperature of the absorption column, more preferably about 100° C. above the temperature of the absorption column. Stripper (c2) preferably is capable of operating at a temperature in the range of 120 to 250° C. Heater (c27) is preferably capable of raising the temperature of the spent pre-washing liquid to such a temperature. In a preferred embodiment, unit (c2) is designed to operate at reduced pressure compared to unit (c1).

The loaded tar stripping gas that is issued from gas outlet (c23) may be discarded from the system or recycled to a gasification or pyrolysis reactor (e), in case such a reactor is comprised in the system, as described below or fed to a tar separation module wherein the tar-like components are separated from the tar stripping gas. The loaded tar stripping gas be recycled to reactor (e), e.g. as feedstock to convert the tar-like components into valuable compounds for e.g. SNG, or as fuel for heating the reactor, wherein outlet (c23) is in fluid connection with inlet (e1) or a further inlet (e2) of reactor (e). The connectivity between outlet (c23) and the inlet of the gasifier may contain a pump (c30). In case the loaded tar stripping gas is used as feedstock in a gasifier, outlet (c23) is in fluid connection with inlet (e1) for receiving feedstock such as biomass of the gasifier (e). In case the loaded tar stripping gas is used as fuel in a gasifier, outlet (c23) is in fluid connection with an inlet of the furnace or combustor that is used to maintain elevated temperature within the gasifier (e). In an especially preferred embodiment, the system is designed as such that the loaded tar stripping gas may be fed either to the feedstock inlet or the furnace inlet, depending on the conditions (e.g. the temperature) within the gasifier.

In case the loaded stripping gas is fed to a tar separation module, outlet (c23) is in fluid connection with an inlet of the tar separation module, whose connection may contain a pump. Such a tar separation module typically further comprises means for separating the tar-like components from the tar stripping gas, an outlet for discharging the cleared tar stripping gas and an outlet for discharging the tar-like components. The means for separating may be a condenser, wherein the loaded tar stripping gas is cooled and at least the tar-like components are condensed, and which is preferably a cooler optionally in combination with a pressurising device. The outlet for discharging the cleared tar stripping gas is preferably in fluid connection with inlet (c22), optionally via a heater that is capable of vaporizing the tar stripping gas, to enable reuse of the tar stripping gas in unit (c2). The tar-like components issued from the tar separation module may be used as deemed fit, such as discarded from the system.

Cooler (d1), Heater (d2) and Ammonia Removal Unit (d3)

Upstream of inlet (a1) may advantageously include a cooler (d1), a heater (d2) and/or an ammonia removal unit (d3). Preferably, the fluid connection between outlet (c14) and inlet (a1) comprises such a cooler (d1) and/or an ammonia removal unit (d2). The presence of a cooler, which may also function as a condenser, is preferred, as it removes the great majority of the water and $NH_3$ (if present) from the gas that is introduced in module (a). The catalyst (a2) may be sensitive to the presence of water and/or ammonia, as it may deactivate.

Cooler (d1) is configured to operate at a temperature and pressure that remove substantially all of the water present in the incoming gas, such as at least 90 vol % or even at least 95 vol %. Typically cooler (d1) is capable of operating at a temperature of 2-50° C., preferably 4-10° C. and at ambient pressure. Such coolers or water condensers are known in the art, and any suitable type can be employed in the system according to the invention. Heater (d2) is advantageously included to ensure that module (a) can be operated at its preferred temperature of 250-650° C.

Subjecting the incoming gas to a cooler already removes most of the ammonia together with the condensed water, but the presence of an ammonia removal unit (d3) may still be preferred.

Ammonia removal units are known in the art, and any suitable type can be employed in the system according to the invention. For example, a washer/scrubber with a nitric acid solution as scrubbing medium can be employed, through which the gas is led. The concentration of nitric acid in the container may for example be 0.5-5 M, preferably about 1 M. However, the inventors have found that the process and system according to the invention is capable of coping with the presence of ammonia without showing any signs of deactivation over the tested period, such that the presence of an ammonia removal unit (d3) may be dispensed with. Hence, in one embodiment, a cooler (d1) is present upstream of inlet (a1), preferably in the fluid connection between outlet (c14) and inlet (a1).

Optional Further Modules

The system according to the invention may further comprise a module (e) for gasifying or pyrolizing coal, biomass, waste or a combination thereof, preferably biomass or (organic) waste. Thus, module (e) is a gasifier (gasification reactor) or pyrolyser (pyrolysis reactor). Such reactors are known in the art. Typically, a flow of biomass and/or coal is introduced into module (e) through an inlet (e1). The gasifying gas can be e.g. air, oxygen and/or steam, which is introduced through the same inlet (e1) or a further inlet. The biomass/waste and/or coal can be further supplied with tar-like components issuing from tar stripping unit (c2) via outlet (c23), i.e. outlet (c23) and an inlet of module (e), e.g. inlet (e1) or a further inlet, are preferably in fluid connection. As such, the tar-like components are recycled and subjected to a further gasification or pyrolysis process, and thus converted in further valuable compounds such as energy gas components and/or monocyclic aromatic compounds. In case module (e) is a gasifier, it is preferably capable of gasifying biomass or waste at a temperature in the range of 600-1300° C. using sub-stoichiometric quantities of oxygen. In case module (e) is a pyrolyser, it is preferably capable of pyrolysing biomass at the same or somewhat lower temperature (e.g. from 450° C. up to 950° C.). As alternative to the embodiment wherein the tar-like components are recycled to reactor (e) itself, the tar-like components may also be used as fuel for heating the reactor (e) to the desired temperature and/or maintaining the reactor (e) at the desired temperature.

Gas issuing from module (e) may be fed to a particulate clearing module (f, wherein particulate material such as dust is removed. Such clearing is preferably based on gravitation and more particularly with a cyclone. Next, the gas, optionally cleared from particulate material, may be treated in a pre-cleaning module (g), especially when the gas contains substantial levels of heavy tar-like components, i.e. having more than 18 ring atoms (i.e. boiling points above about 450° C. at 1 bar), in particular if it contains components of more than 24 ring atoms (i.e. boiling points above about 520° C. at 1 bar). Part or most of these heavy tar-like components may be caught in module (g), such that the gas issuing from said module is depleted in such heavy tar-like components. Besides tars based on hydrocarbons and dust, also sulphur and Cl-containing material can be removed from the gas flow. Module (g) typically employs an aromatic hydrocarbon based liquid to cool the gas and condense tar-like components, which are collected and subsequently separated from the hydrocarbon liquid. Module (g) preferably operates at a higher temperature than unit (c1), for example a liquid inlet temperature of between 150 and 300° C., and a gas inlet temperature between 250° C. and 900° C. In an optional next step, the (partly cleaned) gas may pass through a filter (h), for example an electrostatic precipitator, which removes aerosols. Instead of scrubber (g) and/or filter (h), an alternative tar and dust removing step may be inserted, such as an aerosol scavenger. Then, the gas can be entered into the system of the invention through inlet (a1) of unit (a) or optionally through inlet (c11) of unit (c1).

The optional preceding modules (e), (f), (g) and (h) are only schematically depicted in FIG. 1A. More details are given in WO 2008/010717 and WO 2011/037463. Depending on the quality of the input gas, one or more or all of the intermittent cleaning steps and modules described above can be dispensed with.

DESCRIPTION OF THE FIGURES

FIG. 3 shows the concentrations [C] of CO, $H_2$, $CO_2$ and $CH_4$, FIG. 4 shows the concentrations of $C_2H_x$ (x=2, 4 or 6) and FIG. 5 of $C_2H_4$ [E], benzene [B] and toluene [T].

FIG. 8 depicts the inlet and outlet concentrations of ethylene [E], benzene [B] and toluene [T]. FIG. 9 depicts the concentrations of $C_2H_x$ (x=2, 4 or 6) and FIG. 10 the concentrations [C] of CO, $H_2$, $CO_2$ and $CH_4$.

In FIG. 12, the selectivities to benzene (FIG. 12A) and toluene (FIG. 12B) are shown, and in FIG. 13 the selectivities to benzene+toluene (FIG. 13A) and ethane (FIG. 13B).

EXAMPLES

The examples below demonstrate the invention. In Example 1, ethylene present in a product gas is successfully converted into BTX. In Example 2, a BTX fraction is successfully isolated from a product gas. Example 3 describes the performance of aromatic harvesting by the BTX scrubbing unit. Example 4 illustrates the performance of the aromatization catalyst in a duration test.

Example 1

Experimental

The GaZSM-5 catalysts were prepared by slurry wet impregnation of $NH_4$—ZSM-5 ($SiO_2/Al_2O_3$ molar ratio=30, CBV 3024E Zeolyst International) with aqueous solutions containing the appropriate amount of $Ga(NO_3)_3$ (Alfa Aesar, 99.9%). Catalyst loadings of ca. 0.5 and 2.5 wt % Ga were prepared. The resulting materials were vacuum dried (70 mbar) for overnight at 60° C. and further calcined at 550° C. for 5 h. All the catalysts were pelletized and sieved to 40/70 mesh before testing.

The reactor loaded with the catalyst was heated to 500° C. at a heating at a rate of 2° C./min under 0.5 L/min of a gas mixture composed of 60 vol. % $H_2$ in $N_2$. The $H_2/N_2$ activation gas was applied overnight. After intermediate $N_2$ flushing, 0.5 L/min air was applied for 0.5 hours. After flushing again the reactor with $N_2$, product gas from a MILENA gasifier, cleaned by an OLGA tar removal system and a gas cooler, was fed to the reactor. The 25 kWth MILENA gasifier (see: C. M. van der Meijden, Development of the MILENA gasification technology for the production of Bio-SNG. PhD. Thesis, 2010) was operated under the following operating conditions: ~5 kg/h beech wood as biomass fuel, olivine as bed material, ~850° C. gasification temperature, 1000 g/h steam fluidization, and 10 NmL/min neon injected as tracer gas in the settling chamber of the gasifier. The gasification system operated at atmospheric pressure. A slipstream of about 1 $Nm^3/h$ dry gas from MILENA was directed to the system downstream. OLGA (see: Dahlman Renewable Technologies, OLGA technology (2013); http://www.royaldahlman.com/renewable/home/tar-removal/olga-technology). After OLGA tar removal, most of the water contained in the gas was removed in a gas cooler operating at 5° C. Although about 90% of the ammonia contained in the gas is removed in the condensed water, the remaining traces of ammonia in the feed gas were further removed in a flask containing a 1 M nitric acid solution.

Figure 1A:
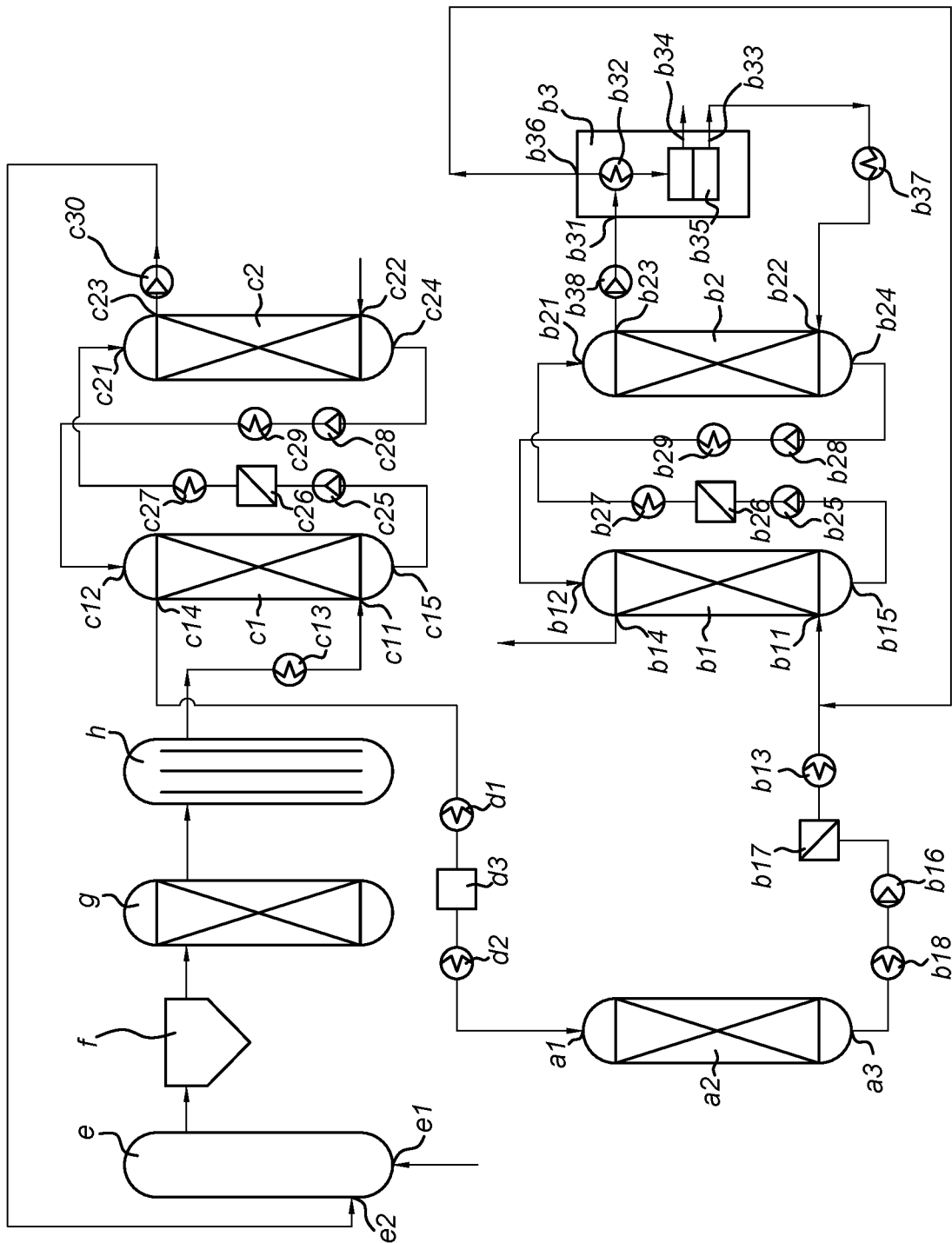
FIG. 1A depicts a preferred embodiment of the process and system according to the invention, with reference to the description of the system above and accompanying reference numbers.
Figure 1B:
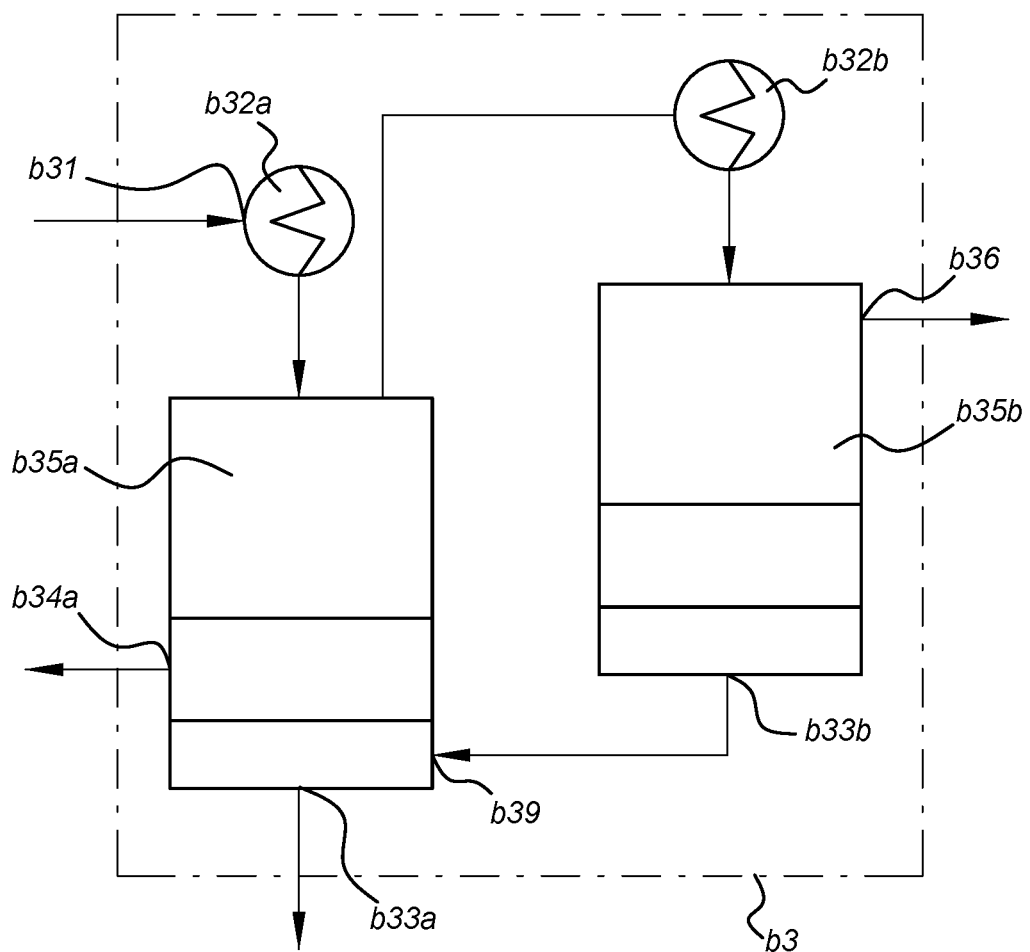
FIG. 1B depicts a preferred embodiment of separation module (b3), with reference to the description of the system above and accompanying reference numbers.
Figure 2:
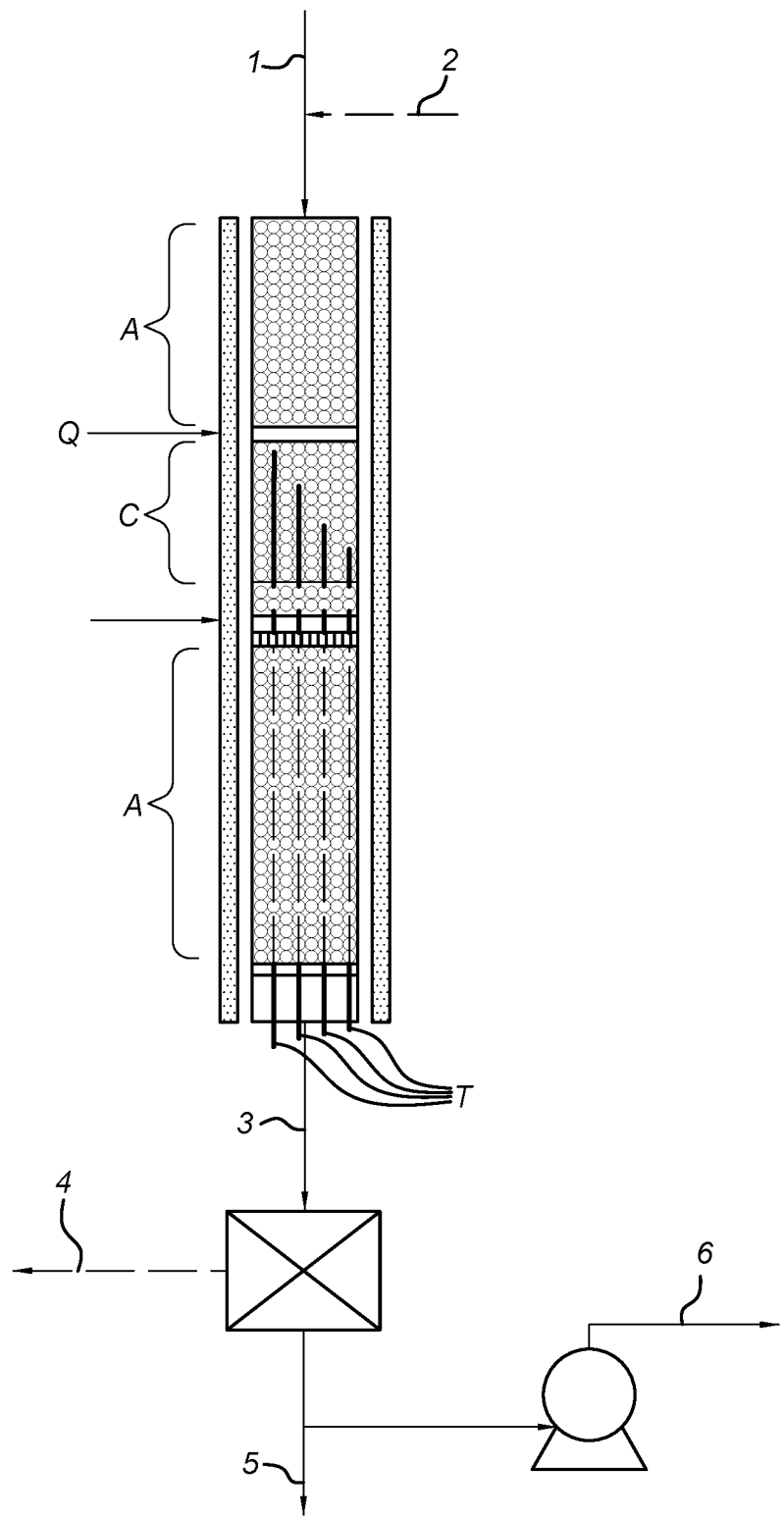
FIG. 2 depicts the configuration inside the reactor used in Example 1. (A) alumina beads; (Q) quartz wool; (C) catalyst material; T=temperature indicators; (1) feed gas; (2) $N_2/H_2/$air inlet; (3) outlet gas; (4) condensate; (5) remaining gas to the afterburner; (6) dry gas to gas analysis.

The Ga-zeolite catalyst materials were tested in terms of activity and stability under relevant gasification conditions. The experiments were carried out in an oven fixed-bed reactor (28 mm diameter, 600 mm height) surrounded by an electrical oven. In all tests, both the height of the catalyst bed was set at 6 cm (20 g of catalyst), and the gas flow to 0.5 L/min (at atmospheric pressure) to keep the gas velocity similar. The configuration of the catalyst inside the reactor is plotted in FIG. 2. Above the catalyst bed (C), alumina beads (A) are placed for feed gas preheating. Four thermocouples (T) measure the temperature profile within the catalyst bed. Pressure indicators located before and after the reactor track the pressure drop over the bed. The gas composition at the inlet and outlet of the reactor was online measured using micro-GC analysis (Varian CP4900, with 3 columns with corresponding TCD detectors).

From the molar balances performed over the reactor, several parameters have been calculated in order to assess the performance of the catalysts. Firstly, ethylene conversion is defined as:

$$\text{Ethylene conversion}(\%) = \frac{\dot{n}_{C_2H_4,in} - \dot{n}_{C_2H_4,out}}{\dot{n}_{C_2H_4,in}} \times 100$$

where $\dot{n}$ is the molar flow in mol/h. The inlet value has been taken in all cases as the last micro-GC analysis before switching to the outlet gas composition. On the other hand, carbon selectivity, i.e. the increase in the content of carbon contained in the product compound of generic formula $C_xH_y$, with respect to the total amount of carbon converted from ethylene and acetylene, has been evaluated according to:

$$\text{Carbon selectivity to product } C_xH_y(\%) = $$
$$\frac{x(\dot{n}_{C_xH_y,out} - \dot{n}_{C_xH_y,in})}{2(\dot{n}_{C_2H_4,in} - \dot{n}_{C_2H_4,out}) + 2(\dot{n}_{C_2H_4,in} - \dot{n}_{C_2H_4,out})} \times 100$$

where $\bar{n}_i$ represents the molar flow of compound i in the gas (in mol/h), and x is the number of moles of carbon contained in the generic compound with formula $C_xH_y$.

Results

Figure 3:
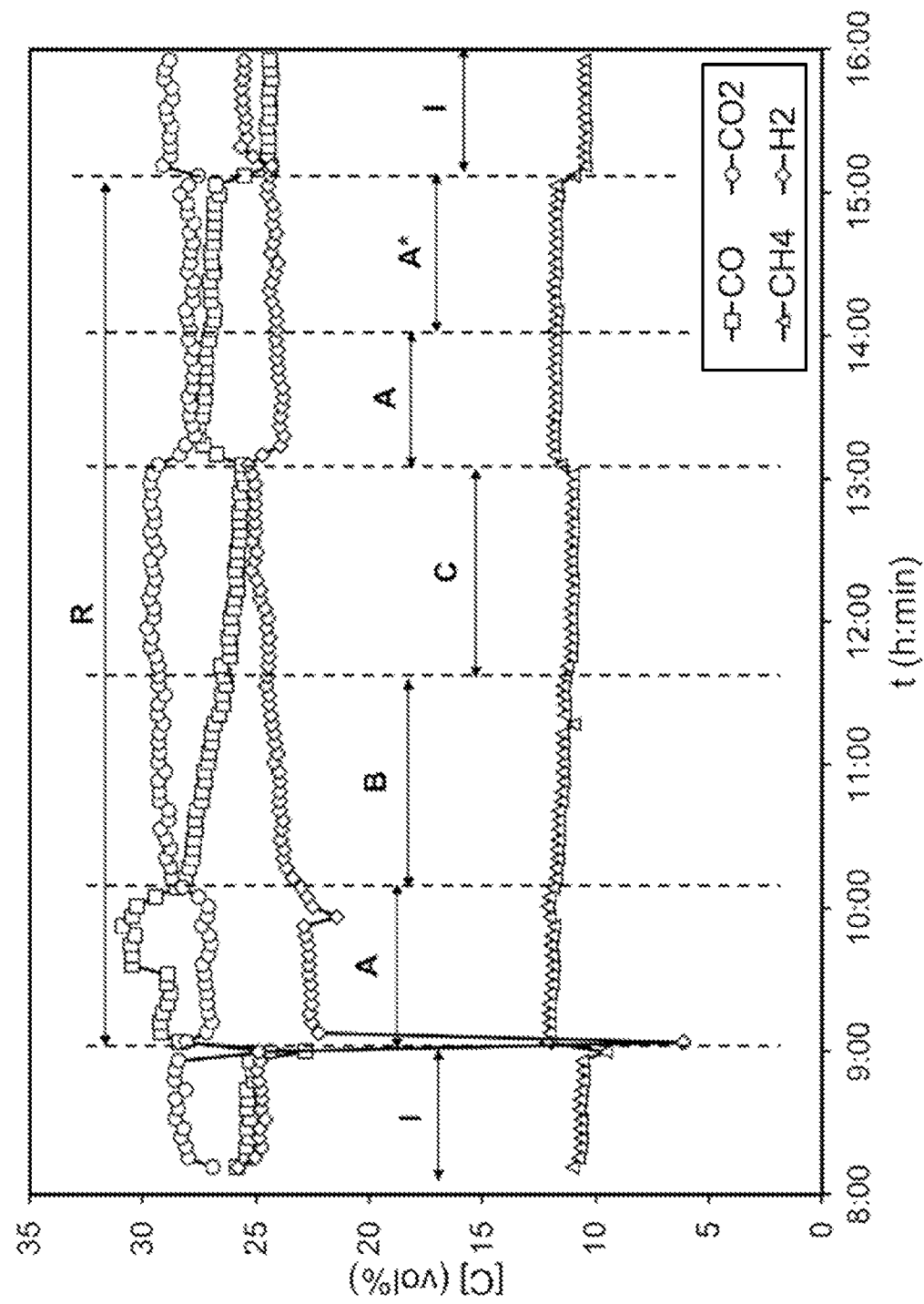
FIGS. 3-5 depict the effects of temperature on inlet and outlet concentrations (in vol %, based on dry volume), as obtained in Example 1. (I) inlet gas; (A) reactor at 500° C.; (B) reactor at 400° C.; (C) reactor at 300° C.; (A*) reactor at 500° C. with $NH_3$ present in the feed.
Figure 4:
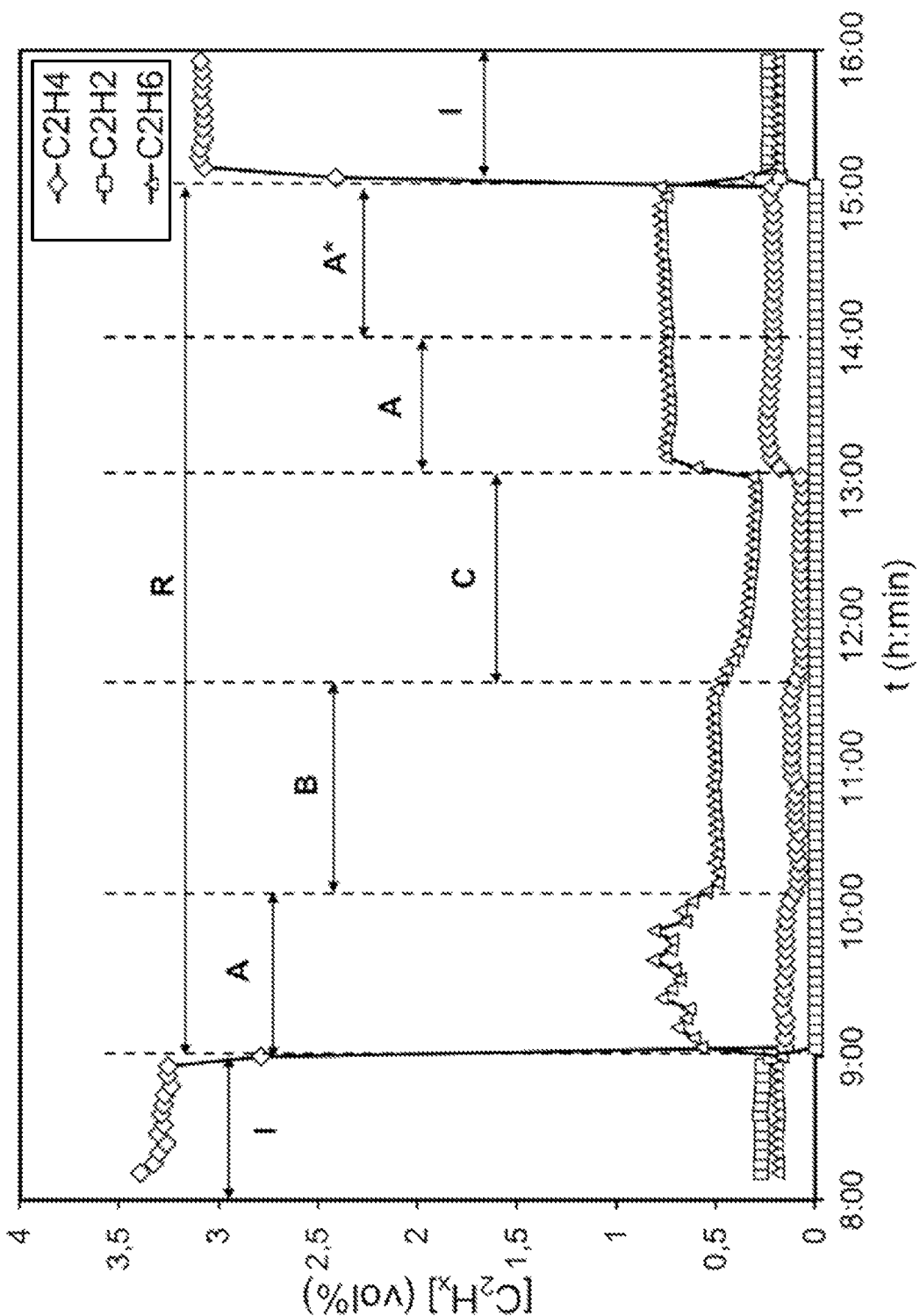
Figure 5:
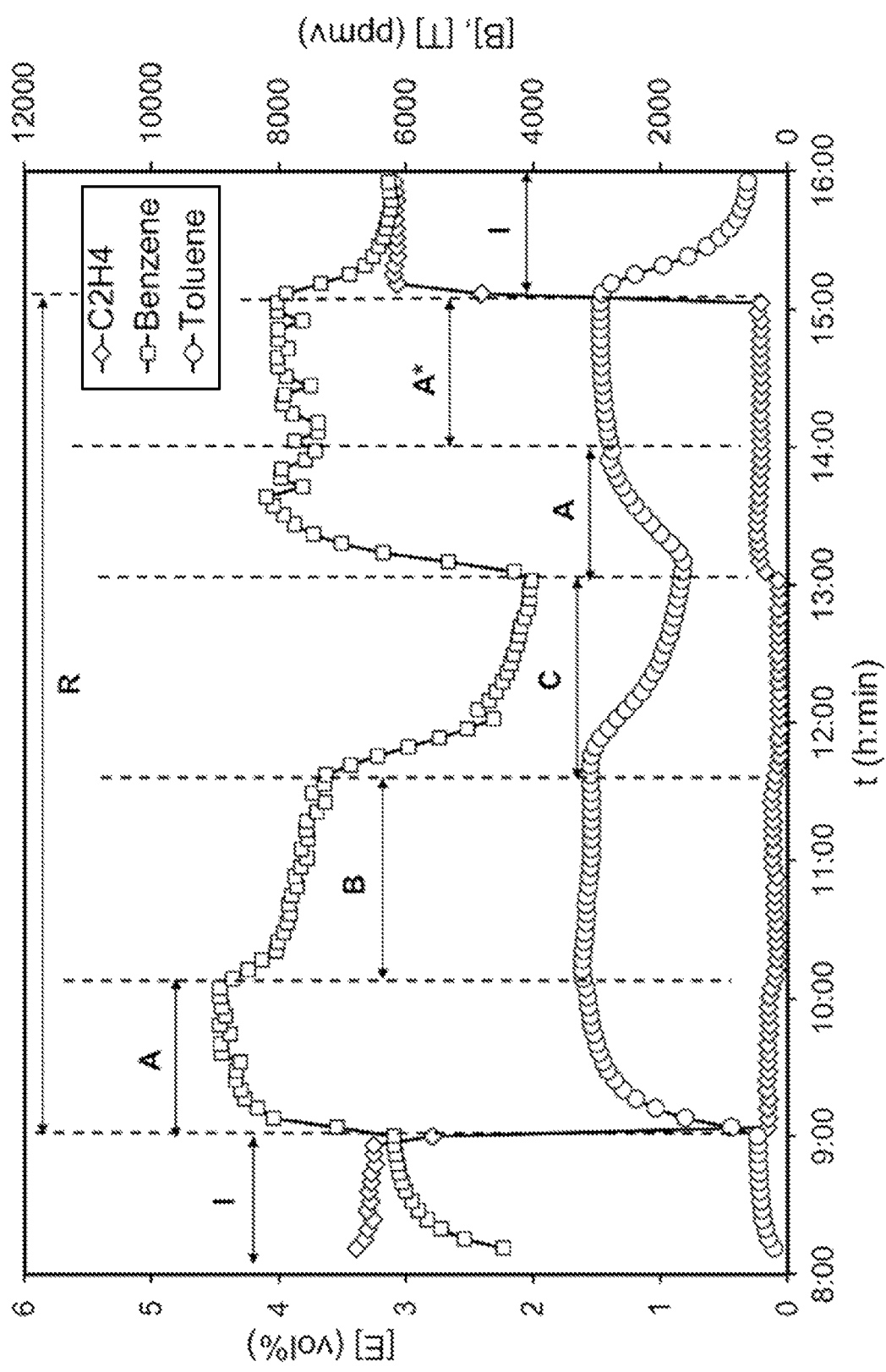

The catalyst containing 2.5 wt. % Ga was analysed at a temperature of 300° C.-500° C. FIG. 3 presents the concentration of the main compounds in the product gas (CO, $CO_2$, $H_2$, and $CH_4$). An initial shift was observed toward higher CO, and lower $CO_2$ and $H_2$ concentrations. Since the water content of the feed gas is very low—most of the water has been previously removed in the gas cooler—the water gas shift reaction is shifted toward the formation of CO and $H_2O$. Lower temperatures favour the rate of the direct water-gas shift reaction. Towards the end of the test, a final stage wherein $NH_3$ is present in the feed was briefly tested at 500° C. No hints of deactivation were detected. FIG. 4 displays the results of the $C_2H_x$ concentration in the inlet and outlet gases. Complete conversion of acetylene was achieved, regardless of the reaction temperature. This is consistent with its highest reactivity among $C_2H_x$ compounds. Moreover, lower temperatures lead to higher ethylene conversion, but lower ethane production. Ethane and methane might be by-products of the hydrogen-transfer mechanisms, in which the formation of diene, cyclic diolefins and aromatics is balanced by the formation of alkanes. The concentration of benzene and toluene in the outlet gas as well as the concentration of ethylene at various reaction temperatures, compared with the inlet gas concentrations, is depicted in FIG. 5. Benzene and toluene show distinct trends. A lower reactor temperature clearly reduces the benzene concentration in the outlet gas, showing that benzene production is favoured at higher temperatures. However, the decrease of toluene concentration is only evident when decreasing the temperature from 400° C. to 300° C. Although lower temperatures lead to lower benzene and toluene production, higher ethylene conversions were observed. Thus, a trade-off occurs between the conversion and selectivity to aromatics. No changes were observed in the gas composition when ammonia was present in the feed gas. The activation energy is highest for the final step of separation between the $Ga^+$ active site and the benzene product, such that the separation process requires high temperature to enhance the reaction rate, which is in consistent with the obtained results. Furthermore, these results indicate different reaction mechanisms and active sites of toluene and benzene. Indeed, toluene formation is not directly related to benzene. In other words, the formation mechanism of toluene does not need benzene as an intermediate, suggesting that their active sites are not at the same location.

Figure 6:
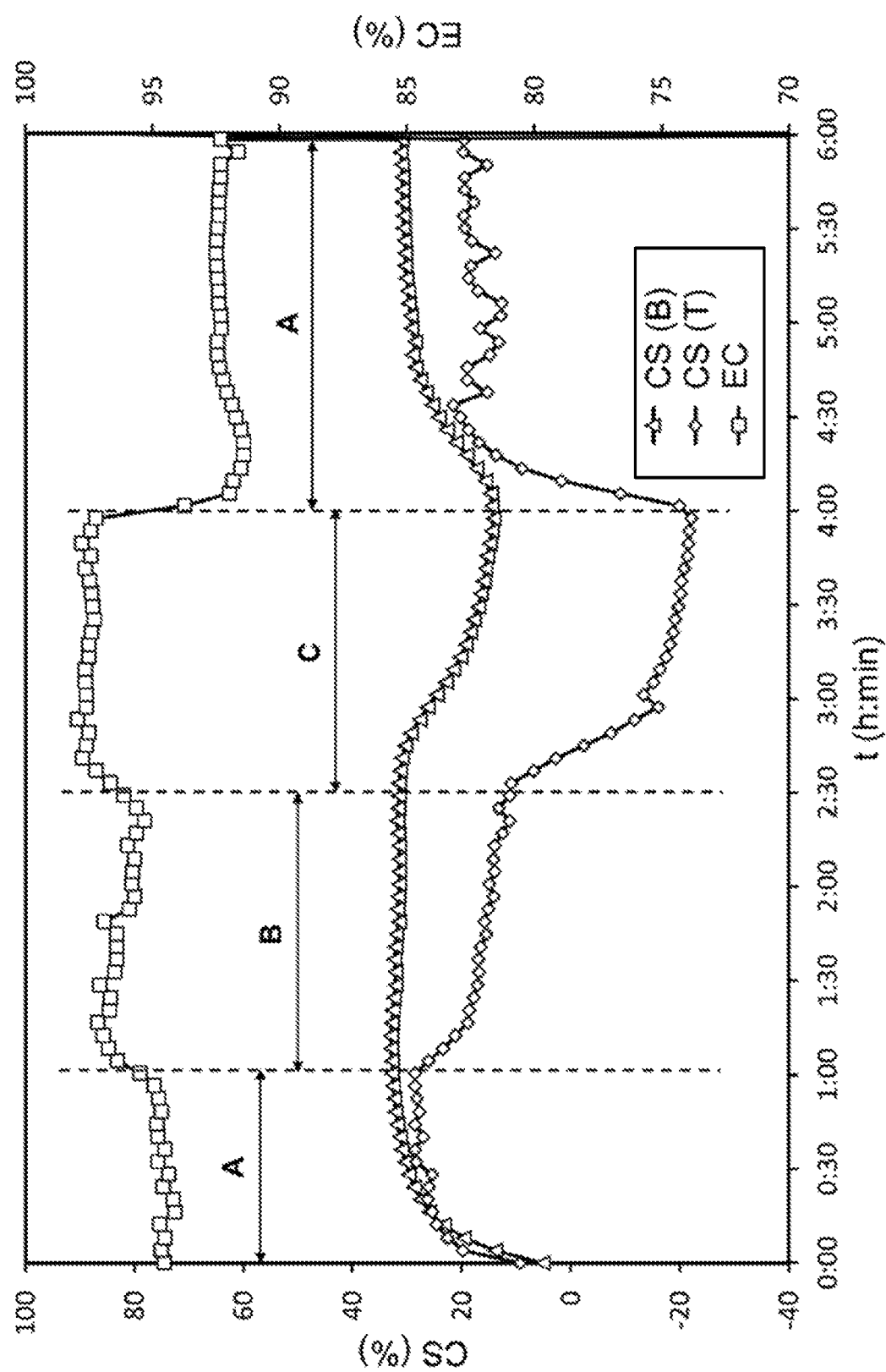
FIG. 6 depicts the effects of temperature on ethylene conversion (EC) and carbon selectivity (CS) to benzene (B) and toluene (T), as obtained in Example 1. (A) reactor at 500° C.; (B) reactor at 400° C.; (C) reactor at 300° C.

FIG. 6 summarizes the effects of the reactor temperature on the conversion and carbon selectivity of the 2.5 wt. % Ga-ZSM-5 catalyst. Although decreasing the temperature from 500° C. to 300° C. slightly increases the ethylene conversion from 95% to 97%, it also results in lower carbon selectivity to aromatics. The carbon selectivity to benzene decreases from about 30% to even negative values when the temperature was decreased from 500° C. to 300° C., whereas the lowering of selectivity to toluene becomes evident when the temperature was decreased from 400° C. to 300° C., with values halving from over 30% to about 15%. These results mean that the composition of the fraction of monocyclic aromatic compounds can be fine-tuned by varying the conditions employed in step (a). Further, it is noteworthy observing that the $NH_3$ content in the feed gas (tested during the last 500° C. stage) did not seem to affect the catalyst performance.

Figure 7:
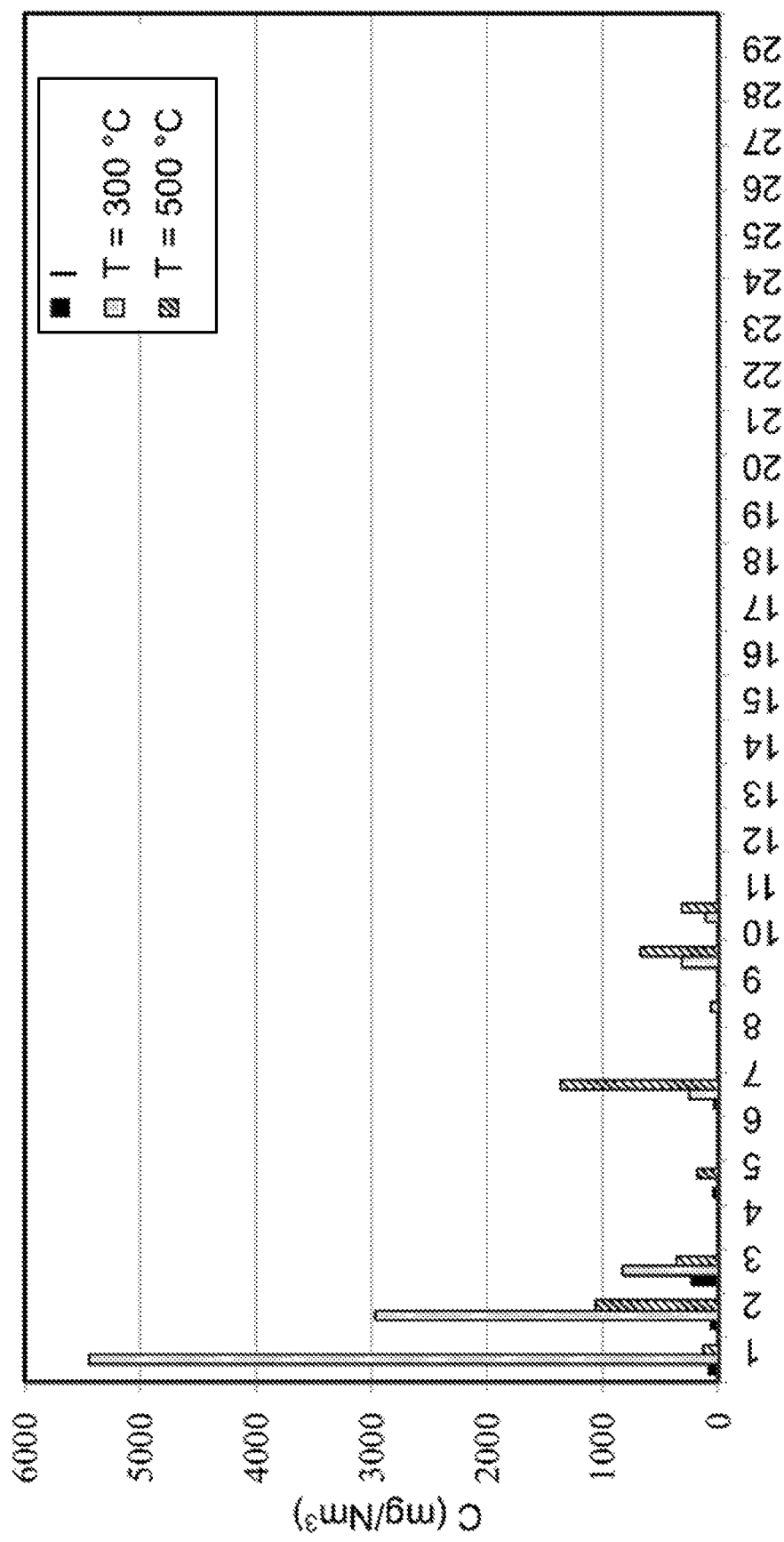
FIG. 7 shows the effect of temperature on the concentration [C] in $mg/Nm^3$ dry gas of aromatic compounds other than benzene and toluene in the inlet gas (I) and outlet gas (T=300° C.; T=500° C.) measured by SPA analysis, as obtained in Example 1. (1) ethylbenzene; (2) m/p-xylene; (3) o-xylene+styrene; (4) phenol; (5) indene+o-cresol; (6) m/p-cresol; (7) naphthalene; (8) quinolone; (9) isoquinoline; (10) 2-methylnaphthalene; (11) 1-methylnaphthalene; (12) biphenyl; (13) 2-ethylnaphthalene; (14) acenaphtylene; (15) acenaphtene; (16) fluorine; (17) phenanthene; (18) anthracene; (19) pyrene; (20) benzo(a)anthracene; (21) chrysene; (22) benzo(b)fluoranthene; (23) benzo(k)fluoranthene; (24) benzo(e)pyrene; (25) benzo(a)pyrene; (26) indeno(123-cd) pyrene; (27) dibenz(ah)anthracene; (28) benzo(ghi) perylene; (29) coronene.

Complementary to online micro-GC analysis, solid phase adsorption (SPA) analyses were also performed at the inlet and outlet gases under stable conditions for the determination of the content and composition of aromatic compounds which, unlike benzene and toluene, cannot be measured online through micro-GC. However, owing to the high volatility of benzene and toluene in the adsorption cartridge, the SPA quantification of benzene and toluene is not reliable, thus benzene and toluene are not reported in the SPA results. The micro-GC results are used instead for calculations. FIG. 7 shows the SPA results of the inlet gas and the outlet gases at 300° C. and 500° C. The catalytic reaction produces besides benzene and toluene other aromatic compounds such as ethylbenzene, xylenes, indene, naphthalene and methyl naphthalene. Due to the fact that o-xylene and styrene have similar retention times, mass spectrometry (MS) was complementary used to determine the contribution of each species to the peak area. MS analysis revealed that about 80% of the signal detected in the inlet syngas corresponded to styrene (i.e. 20% to o-xylene), whereas about 80% of the signal in the outlet gas corresponds to o-xylene. As can be observed, the reaction temperature influences dramatically the distribution of the aromatic products. Whereas lower temperatures favour the production of ethylbenzene and xylenes, higher temperatures give a slightly higher production of naphthalene and naphthalene derivatives.

Figure 8:
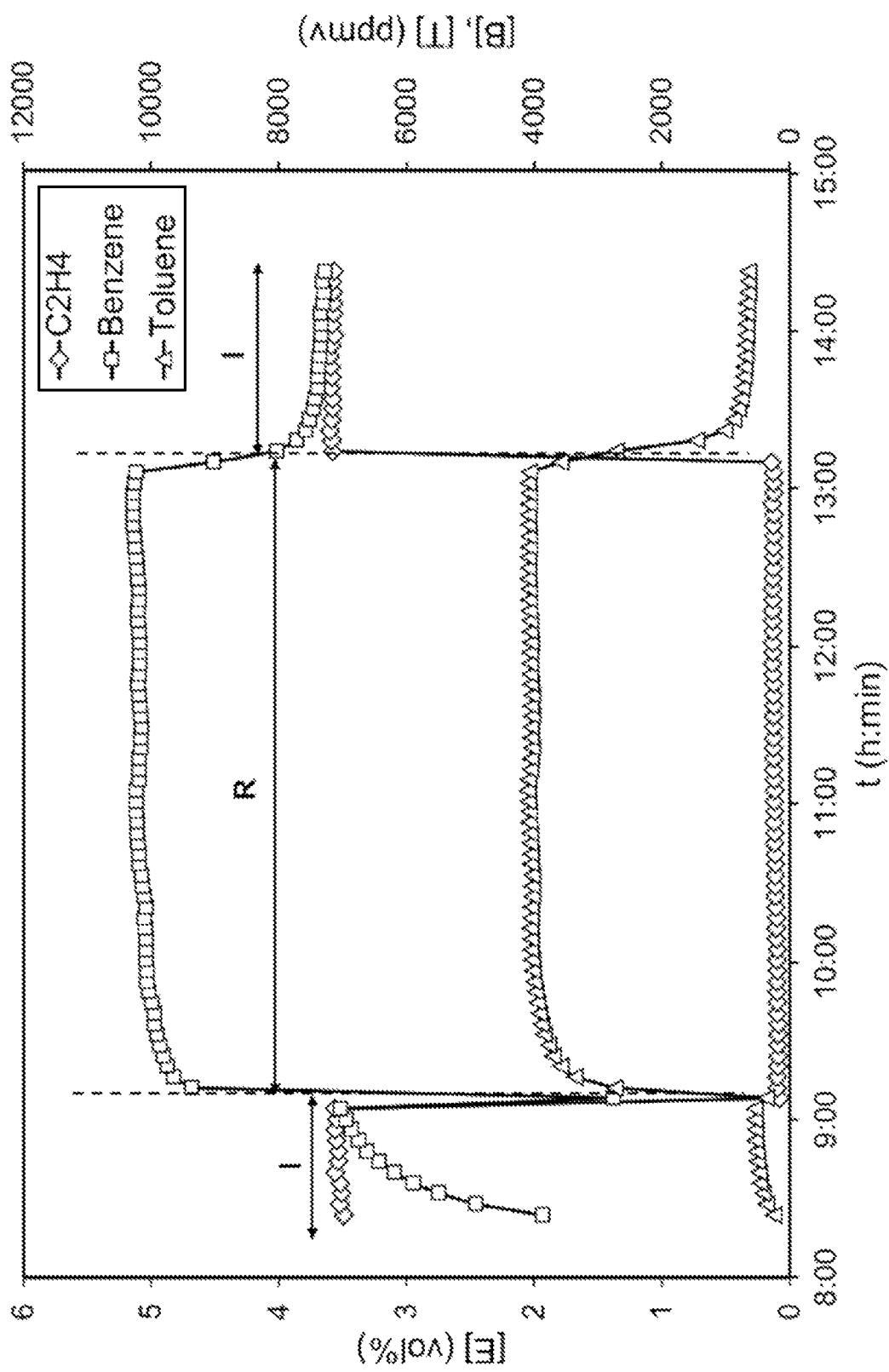
FIGS. 8-10 depict the effects of temperature on inlet and outlet concentrations (in vol %, based on dry volume), as obtained with 2.5% Ga ZSM-5 catalyst in Example 1. (I) inlet gas; (R) reactor in operation.
Figure 9:
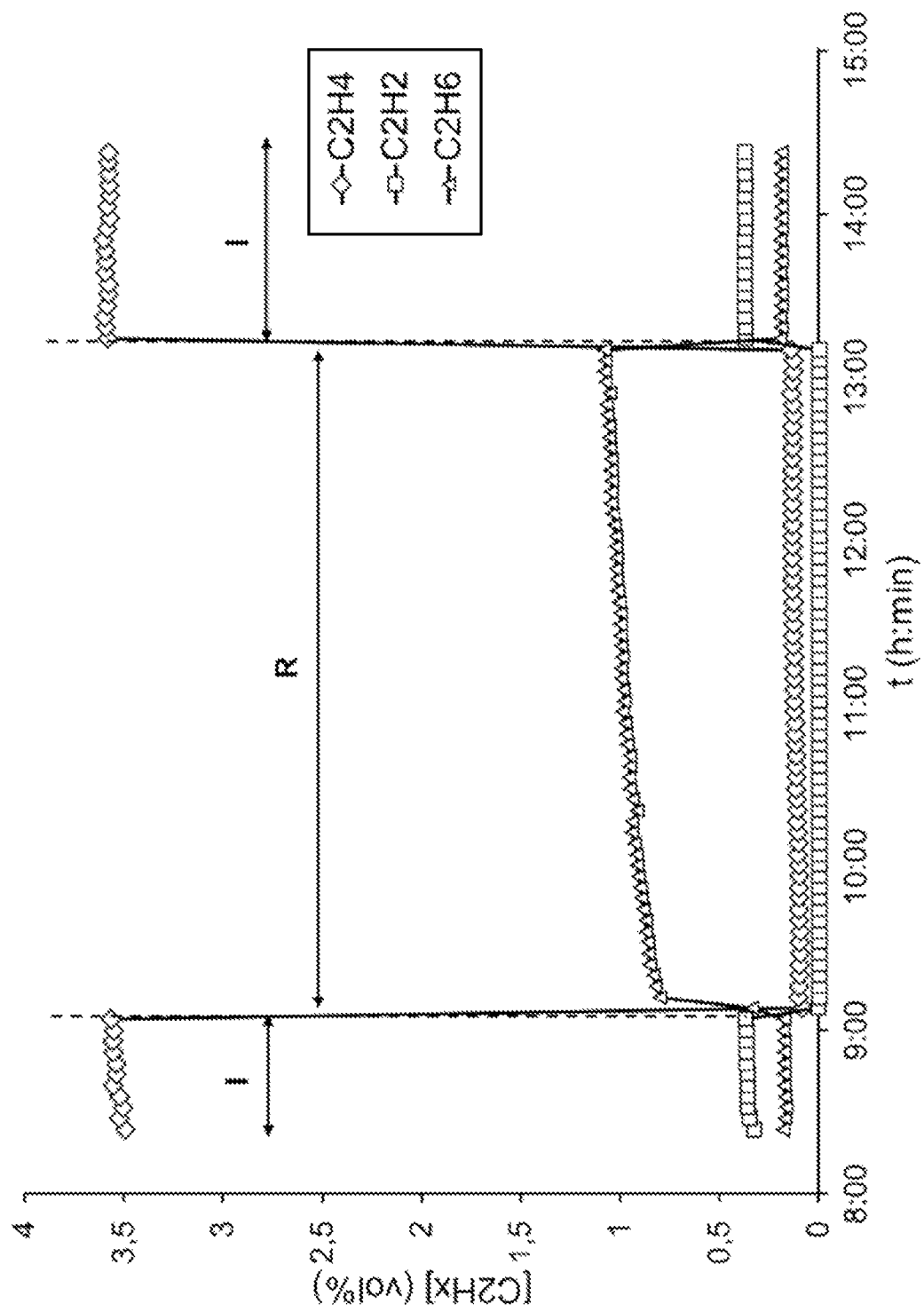
Figure 10:
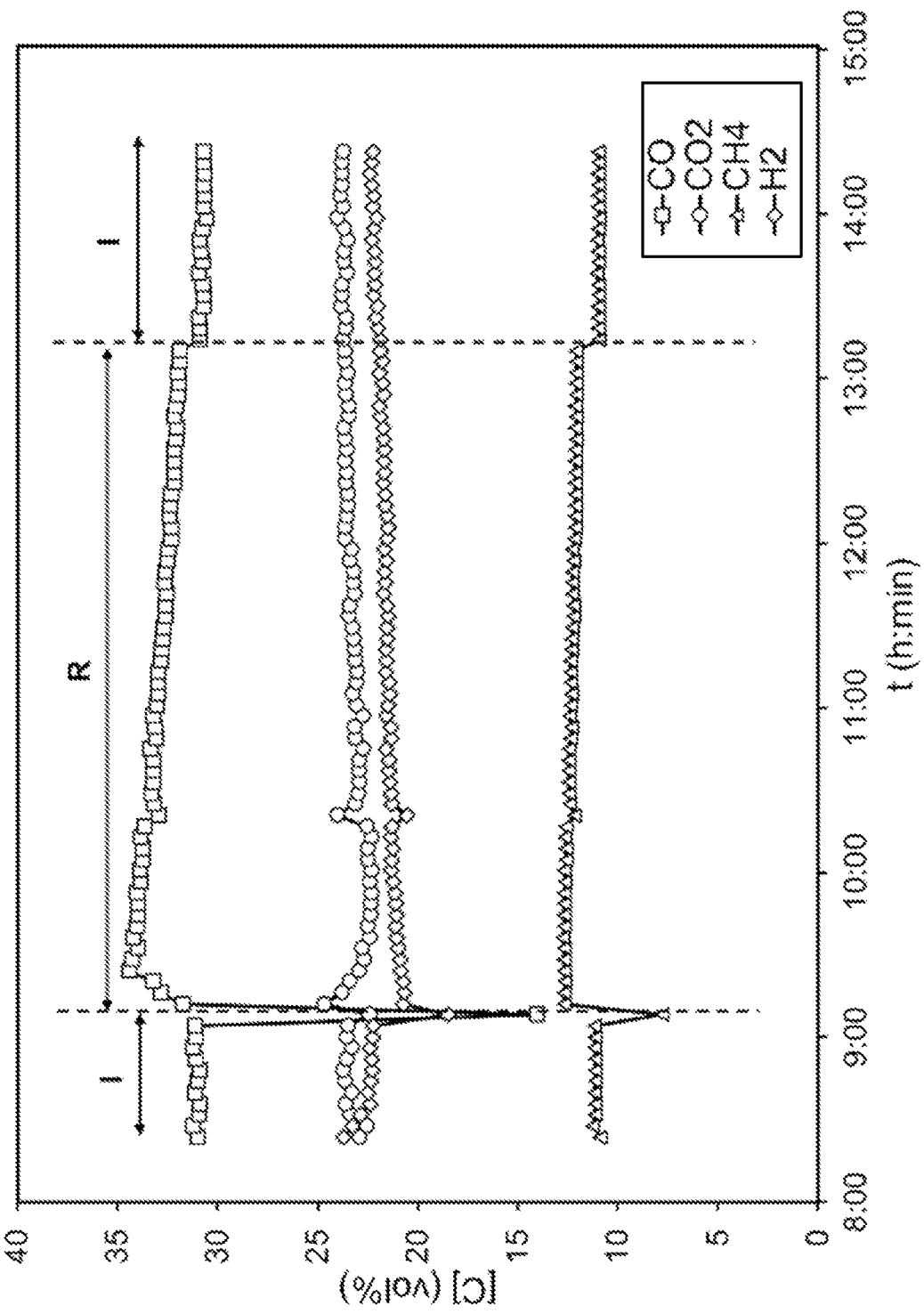

FIGS. 8-10 depict the steady-state situation of a 4-hour run at 500° C. with the 2.5 wt. % Ga-ZSM-5 catalyst. Similar stable conditions were achieved with the other catalyst loadings tested. As can be seen in FIG. 8, the ethylene concentration dropped from 3.5 vol. % dry to <0.1 vol. %, resulting in 97% conversion. The behaviour of the catalyst material was highly stable over the duration of the experiment. The feed product gas composition might lead to milder reducing conditions than, for instance, pure hydrocarbon feeds. Strong reducing atmospheres were reported as a plausible reason for the increased deactivation rate of Ga catalysts. The benzene concentration increased from about 7000 ppmv to over 10000 ppmv, whereas the toluene concentration increased from about 500 ppmv to 4000 ppmv (all concentrations expressed in dry basis). The temperature near the catalyst bed surface increased by about 13° C. upon starting the operation. FIG. 9 shows the complete conversion of acetylene, as well as a marked increase in the ethane concentration from about 0.25 vol. % to more than 1 vol. %, which increased overtime. The concentrations of the major product gas compounds (CO, $H_2$, $CO_2$, and methane), as depicted in FIG. 10, show a shift in the composition upon the start of the reactor operation toward higher CO concentrations and lower $H_2$ and $CO_2$ concentrations, which indicates some transient reverse WGS activity. However, over time $H_2$ and $CO_2$ progressively increase, and CO decreases until recovering similar concentrations to those in the inlet gas. The presence of CO and $CO_2$ in the feed gas may contribute in a positive way to the catalyst stability. This hypothesis is consistent with the mild carbon formation (greyish catalyst) observed during post-inspection. The $CH_4$ concentration slightly increases from 11 vol. % dry to about 12-13 vol. %.

Figure 11:
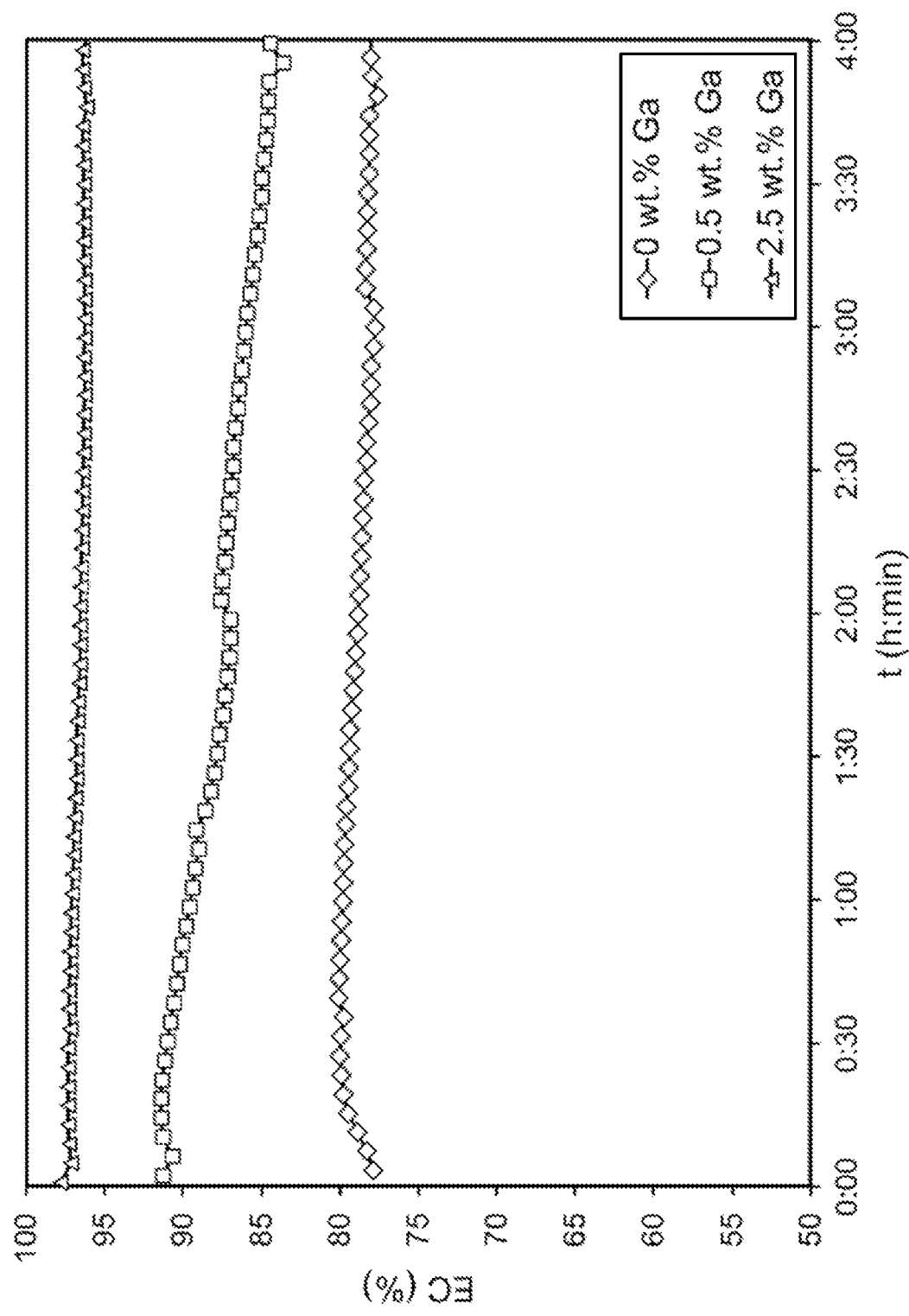
FIG. 11 depicts the effect of the Ga loading on ethylene conversion (EC), as obtained in Example 1.
Figure 12A:
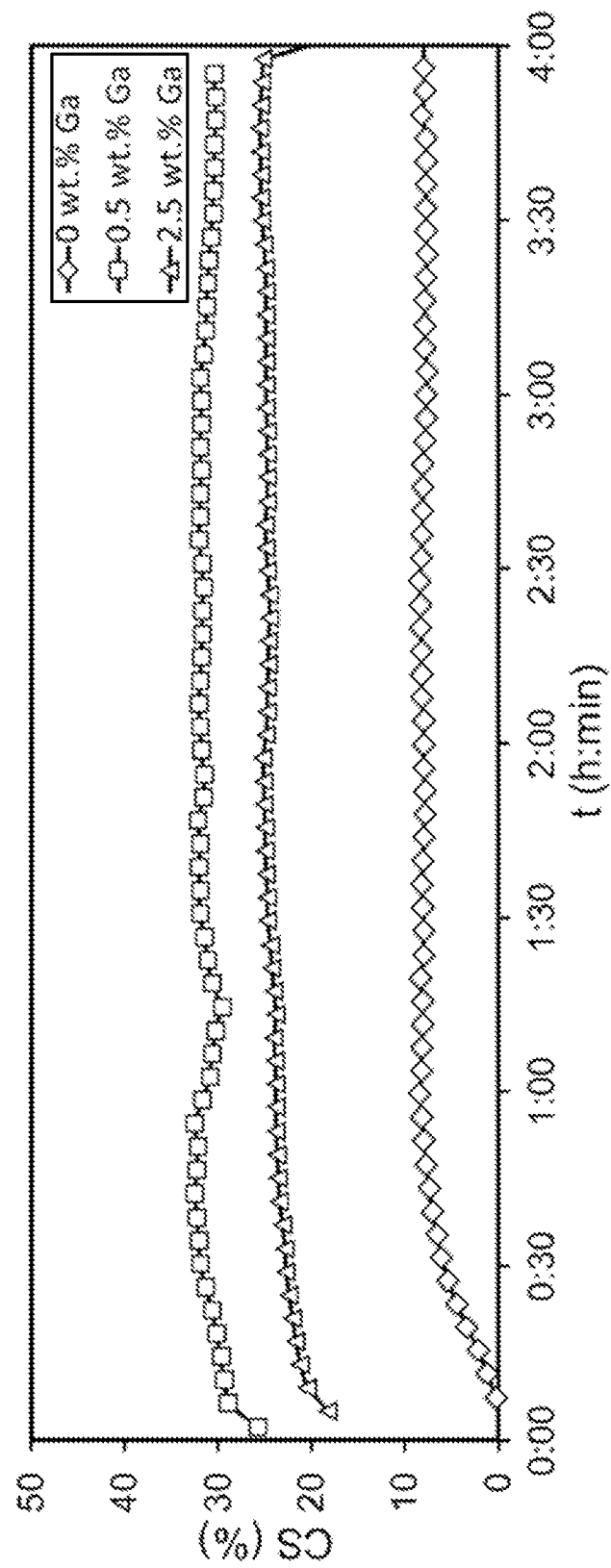
FIGS. 12 and 13 depict the effect of the Ga loading on carbon selectivities (CS), as obtained in Example 1.
Figure 12B:
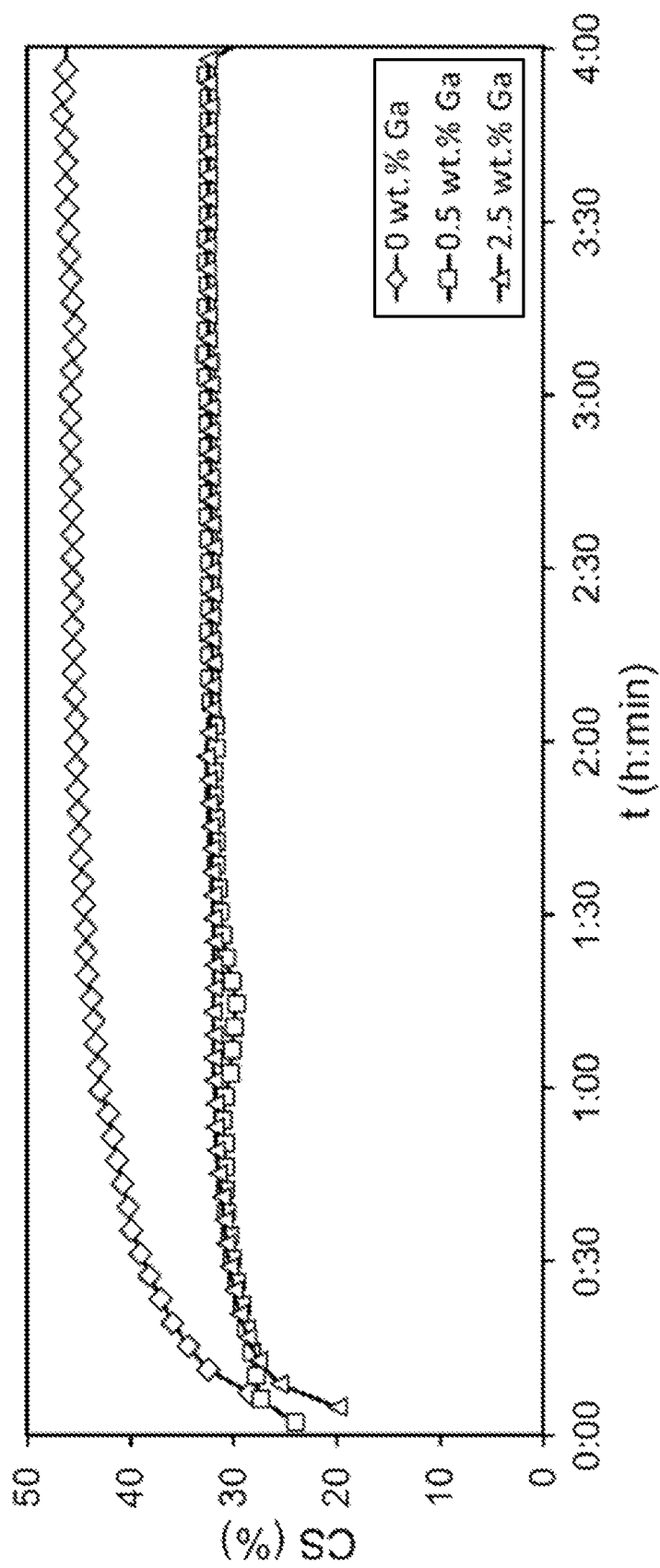
Figure 13A:
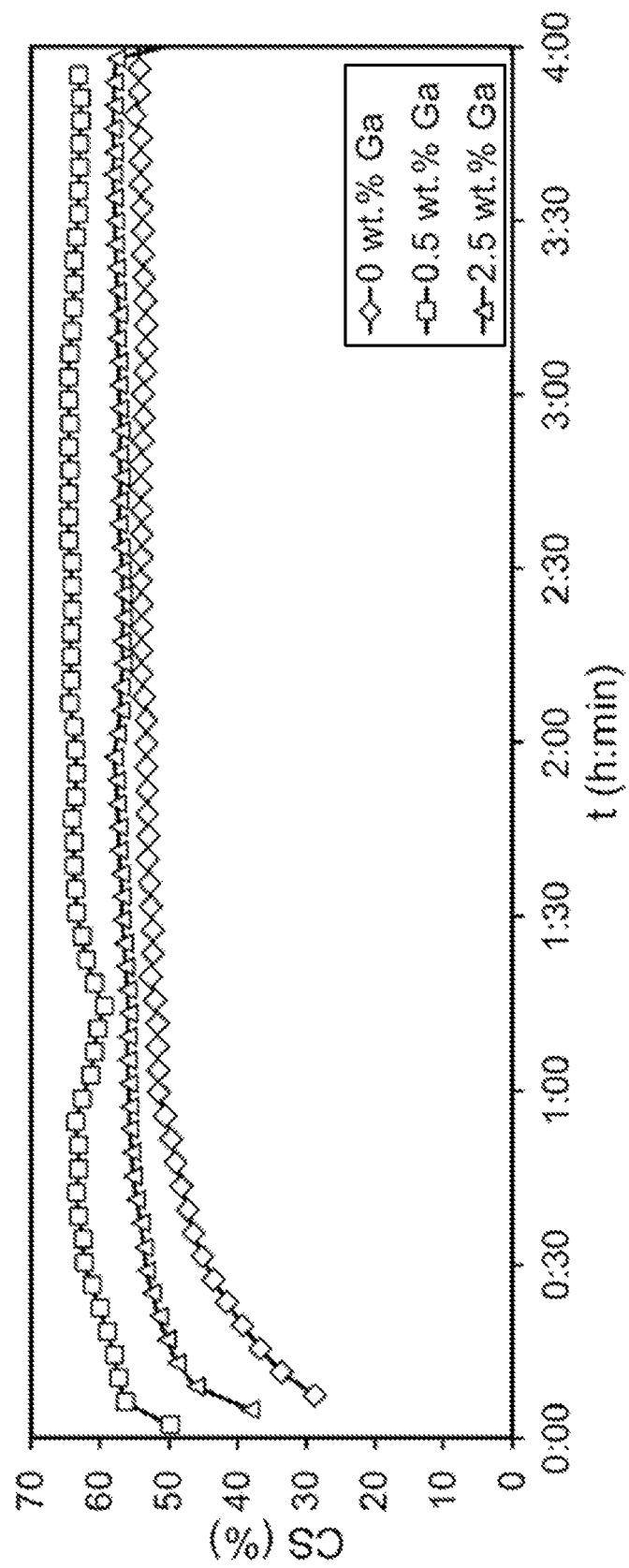
Figure 13B:
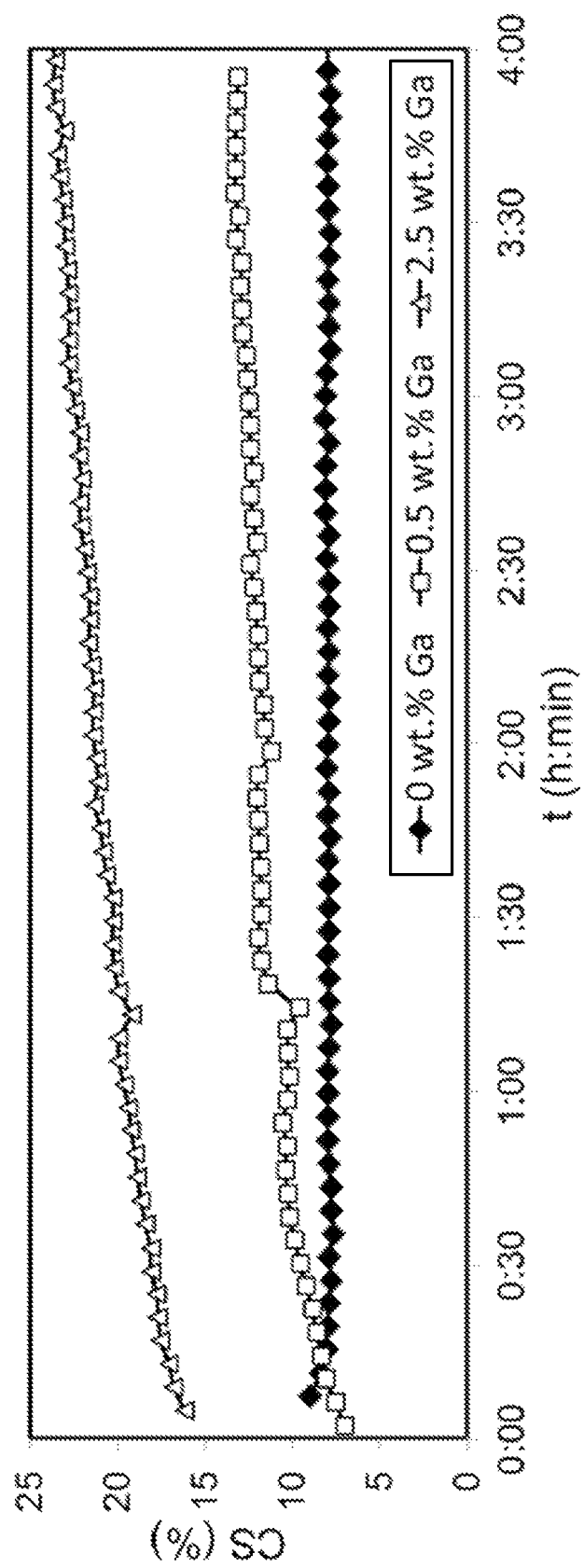

FIG. 11 shows the effect of loading amount of Ga on the conversion efficiency of ethylene. Higher Ga loadings favour ethylene conversion. The reference unloaded zeolite yields ethylene conversion of about 80%. As a comparison, Qiu et al., in *Catal. Letters* 52 (1998) 37-42, reported an ethylene conversion of only 40% at 520° C. with unloaded H-ZSM-5 zeolite by using 3 vol. % ethylene in methane as the feed gas. The highest ethylene conversion value, obtained with 2.5 wt. % Ga-zeolite, was 97%, which is slightly higher than previously reported values by Qiu et al. (93% conversion with 5 wt. % Ga loading). At a Ga loading of 0.5 wt. %, the ethylene conversion can be maintained as high as 85%-90%. Moreover, the 2.5 wt. % Ga— catalyst exhibits a considerably high stability for 4 hours. FIG. 12 shows the results of the effect of Ga loading on the carbon selectivity to benzene and toluene. The carbon selectivity to benzene markedly increases from 8% (zeolite without added Ga) to 32% (0.5 wt. % Ga). In all cases, the catalyst activity remained fairly stable over time. The 0.5 wt. % Ga-catalyst yields the highest selectivity to benzene. Moreover, the zeolite with Ga loading takes approximately 1 hour in stream until reaching stable conditions, whereas the addition of 0.5 wt. % Ga to the zeolite reduces the stabilization time to about 0.5 hour. Therefore, the loaded Ga seems also to improve the catalyst stability. The unloaded ZSM-5 sample exhibits the lowest carbon selectivity to benzene (about 8%), but the highest carbon selectivity to toluene (about 45%). Both the 0.5 wt. % and the 2.5 wt. % Ga catalysts show similar carbon selectivity to toluene (about 30%). FIG. 13A shows the overall carbon selectivity to toluene and benzene. Although the addition of Ga leads to reduced carbon selectivity to toluene, the overall carbon selectivity to toluene and benzene still increases. Ethane formation is favoured at higher Ga contents in the catalyst (see FIG. 13B).

Figure 14:
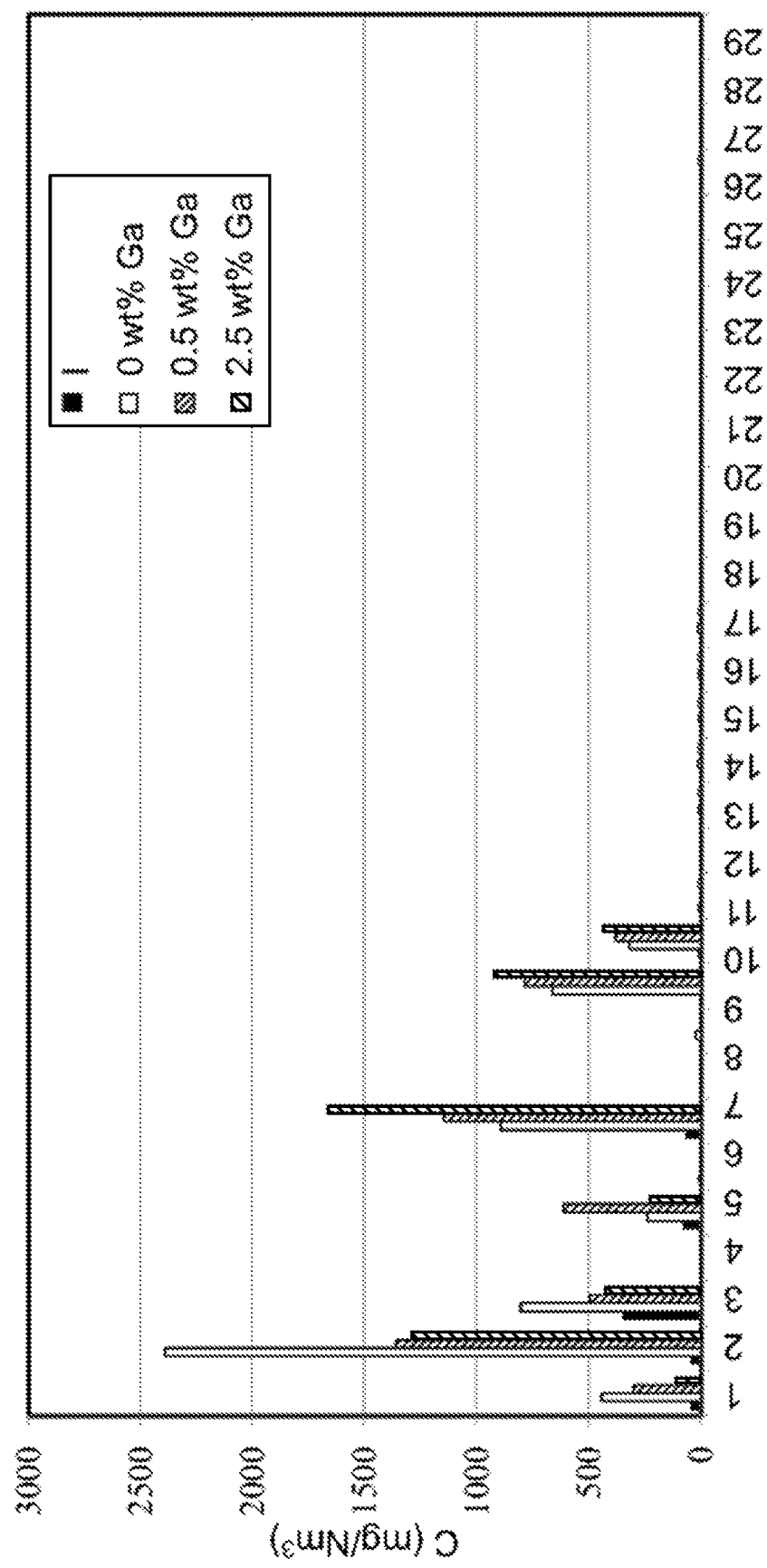
FIG. 14 shows the effect of Ga loading on the concentration [C] in $mg/Nm^3$ dry gas of aromatic compounds other than benzene and toluene in the inlet gas (I) and outlet gas (0 wt %, 0.5 wt % and 2.5 wt % Ga loading) measured by SPA analysis, as obtained in Example 1. (1) ethylbenzene; (2) m/p-xylene; (3) o-xylene+styrene; (4) phenol; (5) indene+o-cresol; (6) m/p-cresol; (7) naphthalene; (8) quinolone; (9) isoquinoline; (10) 2-methylnaphthalene; (11) 1-methylnaphthalene; (12) biphenyl; (13) 2-ethylnaphthalene; (14) acenaphtylene; (15) acenaphtene; (16) fluorine; (17) phenanthene; (18) anthracene; (19) pyrene; (20) benzo(a)anthracene; (21) chrysene; (22) benzo(b)fluoranthene; (23) benzo(k)fluoranthene; (24) benzo(e)pyrene; (25) benzo(a)pyrene; (26) indeno(123-cd)pyrene; (27) dibenz(ah)anthracene; (28) benzo(ghi)perylene; (29) coronene.

FIG. 14 shows the SPA results of the effect of the Ga loading in the ZSM-5 zeolite. It can be observed that the unloaded zeolite exhibits the highest concentrations of ethylbenzene and xylenes in the outlet gas, whereas the addition of Ga to the zeolite favours the formation of benzene and higher hydrocarbons. A maximum overall carbon selectivity to aromatic hydrocarbons of about 73% has been determined for the 0.5 wt. % Ga-zeolite, as reported in the overview of the results in Table 1.

TABLE 1

Summary of effect of Ga loading on ZSM-5 zeolite on the catalyst performance

| Ga loading | $C_2H_4$ conv (%)* | Carbon selectivity (%) | | | | | |
| --- | --- | --- | --- | --- | --- | --- | --- |
| | | Benzene* | Toluene* | Xyl** | EB** | $C_{10}$** | Total Ar*** |
| 0% | 78.9 ± 0.8 | 7.5 ± 1.4 | 43.9 ± 3.2 | 8.7 | 1.3 | 5.6 | 66.9 |
| 0.5% | 87.6 ± 2.2 | 31.4 ± 0.8 | 31.5 ± 1.3 | 4.1 | 0.7 | 5.5 | 73.2 |
| 2.5% | 96.7 ± 0.4 | 24.4 ± 1.1 | 31.8 ± 1.3 | 3.6 | 0.2 | 7.0 | 67.1 |

*From average values measured by online micro-GC analysis.
**From SPA analysis taken under stable conditions (after 2 hours on stream). Xyl = xylenes (o/m/p); EB = ethylbenzene; $C_{10}$ = naphthalene + 1-methyl-naphthalene + 2-methylnaphthalene.
***Total selectivity to aromatic compounds.

CONCLUSIONS

The catalytic conversion of ethylene present in product gas from biomass gasification into aromatics (BTX) using bifunctional Ga-loaded ZSM-5 zeolites as catalyst under realistic gasification conditions has been analysed. The results have shown that ethylene conversion of 80-97% can be achieved. In all cases, acetylene conversion was complete. The carbon contained in ethylene and acetylene is mainly converted to benzene, toluene, ethane and methane. Ethane and methane (favourable compounds in view of bio-SNG production) are intermediate by-products of hydrodealkylation reactions. SPA analysis has revealed the formation presence of other aromatic compounds, namely xylenes, ethylbenzene, naphthalene, and naphthalene derivatives. The addition of Ga to the zeolite significantly improved both the ethylene conversion (90-97%) and the carbon selectivity to benzene. The 0.5 wt. % promoter-zeolite achieved the highest carbon selectivity to benzene (~32%), benzene and toluene (~65%), and total carbon selectivity to aromatics (73%). Moreover, it has been observed that the reaction temperature dramatically influences the distribution of carbon selectivity towards aromatics. Lower temperatures favour the production of ethylbenzene and xylenes, whereas benzene, naphthalene and naphthalene derivatives are promoted at higher temperatures. Based on the results, it is proposed that the formation of benzene and toluene need different active sites. The location of the active sites of ethylene conversion to toluene may be mainly on the surface of zeolite, whereas the active sites for benzene formation may be located in the pores of the zeolite. Moreover, Ga produces a partial replacement of the zeolite acid sites within the pores of the zeolite which eventually modifies the extent of the aromatic interconversion reactions (hydrodealkylation) toward benzene formation.

the combined organic layers is given in Table 2. The average compositions of the gas flows over the complete duration of the experiment, as determined by micro-GC, are given in Table 3.

TABLE 2

Composition of the combined organic layers obtained from the BTX scrubber.

| Compound | First condenser (26° C.) | Second condenser (4-5° C.) | Total |
| --- | --- | --- | --- |
| total (g) | 884.5 | 284.7 | 1169.2 |
| total BTX (g) | 824.6 | 266.8 | 1091.4 |
| benzene (g, wt %) | 753.6 (85.2 wt %) | 258.9 (90.9 wt %) | 1012.5 (86.6 wt %) |
| toluene (g, wt %) | 68.7 (7.77 wt %) | 7.77 (2.73 wt %) | 76.50 (6.54 wt %) |
| xylene (g, wt %) | 2.26 (0.26 wt %) | 0.06 (0.02 wt %) | 2.32 (0.20 wt %) |
| ethylbenzene (wt %) | 0.19 | 0.02 | 0.15 |
| styrene (wt %) | 1.48 | 0.07 | 1.14 |
| cresol (wt %) | 0.37 | 0.00 | 0.28 |
| naphthalene (wt %) | 0.75 | 0.00 | 0.57 |
| further aromatic compounds (wt %) | 0.82 | 0.39 | 0.72 |
| thiophene (wt %) | 0.12 | 0.13 | 0.12 |
| water (wt %) | 0.07 | 0.67 | 0.22 |

Example 2

Beech wood (5 kg/h) was subjected to gasification with 1 kg steam per h in an indirect allothermal biomass gasifier (MILENA), which is coupled to a pre-washing unit (OLGA absorber). A trace amount of argon, which was used as tracker, was added to the gasifier gas, which was fed to the pre-washing unit with an average gas flow of about 15 Nl/min, based on dry gas. The partly cleaned gas was led via a cooler (T=5° C.), a safety filter (soxhlet filter) and glass beads to an absorber (BTX scrubber). The absorber of the BTX scrubber operated at 35° C. and ambient pressure with polymethylphenylsiloxane as a washing liquid. The loaded absorbent was stripped at 120° C. using 205-820 g/h steam. Loaded stripping gas was led to condensers via tubes heated at 120-160° C. The first condenser operated at 25-27° C. and the second condenser at 4-5° C. Liquids were collected from the first condenser, while remaining gases were led to the second condenser. Liquids were collected from the second condenser. The scrubbed gas was subjected to HDS and subsequently steam reforming to obtain a bio-SNG. The experiment was run continuously for 75 hours at ambient pressure.

Collection of liquids occurred by first collecting the aqueous layer by opening a tap at the bottom of the collection flask. Collection of the aqueous layer was stopped just prior to the meniscus reached the tap. An as small as possible mixed fraction was collected and discarded, after which the organic layer was completely drained in a separate flask. A total of 1.17 kg of organic layer was collected (885 g from the first condenser at 26° C. and 285 g from the second condenser at 5° C.) over the complete duration of the experiment, of which 86.6 wt % benzene, 6.5 wt % toluene and 0.20 wt % xylene. A detailed compositional analysis of

TABLE 3

Composition of the gas flows (based on dry volume)

| Component | Gasifier gas [a] | pre-washed gas [b] | purified gas [c] |
| --- | --- | --- | --- |
| inert (vol %) [d] | 3.7 | 4.8 | 5.4 |
| $CH_4$ (vol %) | 11.3 | 10.9 | 10.5 |
| CO (vol %) | 32.0 | 28.9 | 23.7 |
| $CO_2$ (vol %) | 25.3 | 25.0 | 27.1 |
| $C_2$ (vol %) [e] | 3.9 | 3.9 | 3.0 |
| $H_2S$ (ppmV) | 100 | 151 | 88 |
| COS (ppmV) | 3 | 5 | 0 |
| benzene (ppmV) | 8131 | 4680 | 271 |
| toluene (ppmV) | 596 | 261 | 0 |
| thiophene (ppmV) | 20 | 17 | 0.9 |
| tar (mg/Nm³) | 17565 | 680 | 61 |
| $H_2$ (vol %) [f] | 22.9 | 26.0 | 30.0 |

[a] gas emerging from the gasifier, prior to being subjected to pre-washing;
[b] gas emerging from the OLGA absorber, prior to being subjected to the BTX scrubber;
[c] gas emerging from the BTX scrubber;
[d] Ar + $N_2$;
[e] ethane + ethylene + acetylene;
[f] $H_2$ content estimated, based on total volume of 100 vol %.

Tar-like components were mainly removed in the pre-washing step, while monocyclic aromatic compounds, such as benzene, toluene and even thiophene, were largely maintained in the permanent gas stream. The BTX scrubber effectively removed the monocyclic aromatic components. The benzene concentration in the partly cleaned gas emerging from the OLGA absorber was between 4000 and 7000 ppm (vol.), which was lowered to ~300 ppm (vol.) in the gas stream emerging from the BTX-scrubber. The average removal of benzene amounted to 95% using a steam flow of 820 g/h, which reduced to 89% and 87% at a gas flow of 410 g/h and 205 g/h respectively. 100% of the toluene was removed at all gas flows. Only trace amounts of tar-like components were obtained in the organic layers obtained in the first and second condensers.

The composition of the gas was analysed prior to and after the condensers, and the removal percentages obtained during the BTX scrubbing of a variety of compounds are given in Table 4. The aromatic compounds benzene, toluene, xylene and thiophene (and its derivatives) were effectively removed during the BTX scrubbing, wherein generally the highest steam flow provided the highest removal. At the same time, permanent gases such as $C_1$-$C_3$ hydrocarbons (alkanes and alkenes) are effectively retained in the gas stream. Especially methane, CO and $CO_2$ are completely retained. Any transport thereof to the stripping gas is cancelled when the permanent gases are recycled to the entrance of the BTX scrubber. The content of the permanent gases in the fuel gas (at the entrance of the BTX scrubber) and in the permanent gas stream after stripping (downstream of the second condenser) is given in Table 5. In view of its very small volume, nitrogen gas was added to the permanent gas stream to enable measure of its contents (tracer). The amount of these permanent gases that were transported to the stripping gas is also included in Table 5. The permanent gas stream further contained 4.6 vol % benzene (based on the permanent gas stream without added nitrogen).

TABLE 4

Removal percentages for certain compounds (15 NL/min inlet gas)

| Compound | steam flow during stripping | | |
|---|---|---|---|
| | 205 g/h | 410 g/h | 820 g/h |
| Aromatic compounds | | | |
| benzene | 87% | 89% | 95% |
| toluene | 93% | 92% | 100% |
| xylene | 100% | 100% | 100% |
| Sulphur components | | | |
| thiophene | 94% | 91% | 96% |
| 2-methyl-thiophene [b] | 100% | 100% | 100% |
| 3-methyl-thiophene [b] | 100% | 100% | 100% |
| COS | 6% | 0% | 14% |
| methyl mercaptan | 67% | 68% | 60% |
| ethyl mercaptan | 76% | 78% | 77% |

[a] nd = not determined
[b] no methyl-thiophenes were detected after the BTX-scrub.

TABLE 5

Experimentally determined transport values of permanent gases

| Permanent gases | In fuel gas | In strip gas | transported |
|---|---|---|---|
| methane (vol %) | 11.00 | 0.13 | 1.18 |
| ethane (vol %) | 0.20 | 0.0094 | 4.70 |
| ethene (vol %) | 3.10 | 0.168 | 5.43 |
| ethyne (vol %) | 0.155 | 0.0185 | 11.94 |
| $CO_2$ (vol %) | 25.00 | 0.72 | 2.88 |
| CO (vol %) | 28.00 | 0.07 | 0.25 |
| $H_2$ (vol %) | 26.00 | 0.00 | 0.00 |
| $H_2S$ (ppmV) | 150.00 | 63 | 42.00 |
| COS (ppmV) | 5.00 | 0.00 | 0.00 |

The results in Table 4 show that the BTX-scrubber, i.e. step (b) of the process according to the invention, effectively removes a fraction of aromatic compounds, which contains almost exclusively BTX. The BTX fraction can be used as deemed fit, e.g. marketed as bio-based BTX or the like, while the energy gas is sufficiently purified from tar-like components and aromatic components by virtue of the combined pre-washing and BTX-scrubber such that conversion into bio-SNG (or other products) is readily accomplished.

Example 3

Refuse-derived fuel (RDF) (3.9 kg/h) was subjected to gasification with 2 kg steam per h in an indirect allothermal biomass gasifier (MILENA), which is coupled to a pre-washing unit (OLGA absorber). Nitrogen gas was added to the steam flow to maintain sufficient gas flow throughout the system. The gasifier gas was fed to the pre-washing unit with an average gas flow of about 15 Nl/min, based on dry gas. The partly cleaned gas was led via a cooler (T=5° C.), a safety filter (glass beads) and a pre-washing unit to remove tars (washing liquid=polymethylphenylsiloxane; T=80° C., ambient pressure) to an absorber (BTX scrubber). The absorber of the BTX scrubber operated at 35° C. and ambient pressure with polymethylphenylsiloxane as a washing liquid. The loaded absorbent was stripped at 160° C. using 0.25 m³/h steam. Loaded stripping gas was led to condensers via tubes heated at 160° C. The first condenser operated at 25-27° C. and the second condenser at 4-5° C. Liquids were collected from the first condenser, while remaining gases were led to the second condenser. Liquids were collected from the second condenser. A fraction of monocyclic aromatic compounds comprising benzene, toluene and xylene was collected. The experiment was run continuously for 3.5 hours at ambient pressure. The average compositions of the gas flows over the complete duration of the experiment, as determined by micro-GC, are given in Table 6.

TABLE 6

Composition of the gas flows

| Component | Gasifier gas [a] | pre-washed gas [b] | purified gas [c] |
|---|---|---|---|
| inert (vol %) [d] | 51.7 | 53.8 | 53.4 |
| $CH_4$ (vol %) | 7.8 | 7.7 | 7.5 |
| CO (vol %) | 9.0 | 9.0 | 9.0 |
| $CO_2$ (vol %) | 11.4 | 12.2 | 11.2 |
| $C_2$ (vol %) [e] | 7.4 | 7.8 | 7.2 |
| $H_2S$ (ppmV) | 524 | 633 | 449 |
| COS (ppmV) | 9 | 16 | 0 |
| benzene (ppmV) | 9853 | 9135 | 302 |
| toluene (ppmV) | 1490 | 1269 | 35 |
| thiophene (ppmV) | 43 | 29 | nd [f] |
| tar (mg/Nm³) | 38373 | 809 | 61 |
| $H_2$ (vol %) [g] | 8.4 | 8.4 | 8.4 |

[a] gas emerging from the gasifier, prior to being subjected to pre-washing;
[b] gas emerging from the OLGA absorber, prior to being subjected to the BTX scrubber;
[c] gas emerging from the BTX scrubber;
[d] Ar + $N_2$;
[e] ethane + ethylene + acetylene;
[f] not determined;
[g] $H_2$ content estimated, based on total volume of 100 vol %.

Example 4

Figure 15:
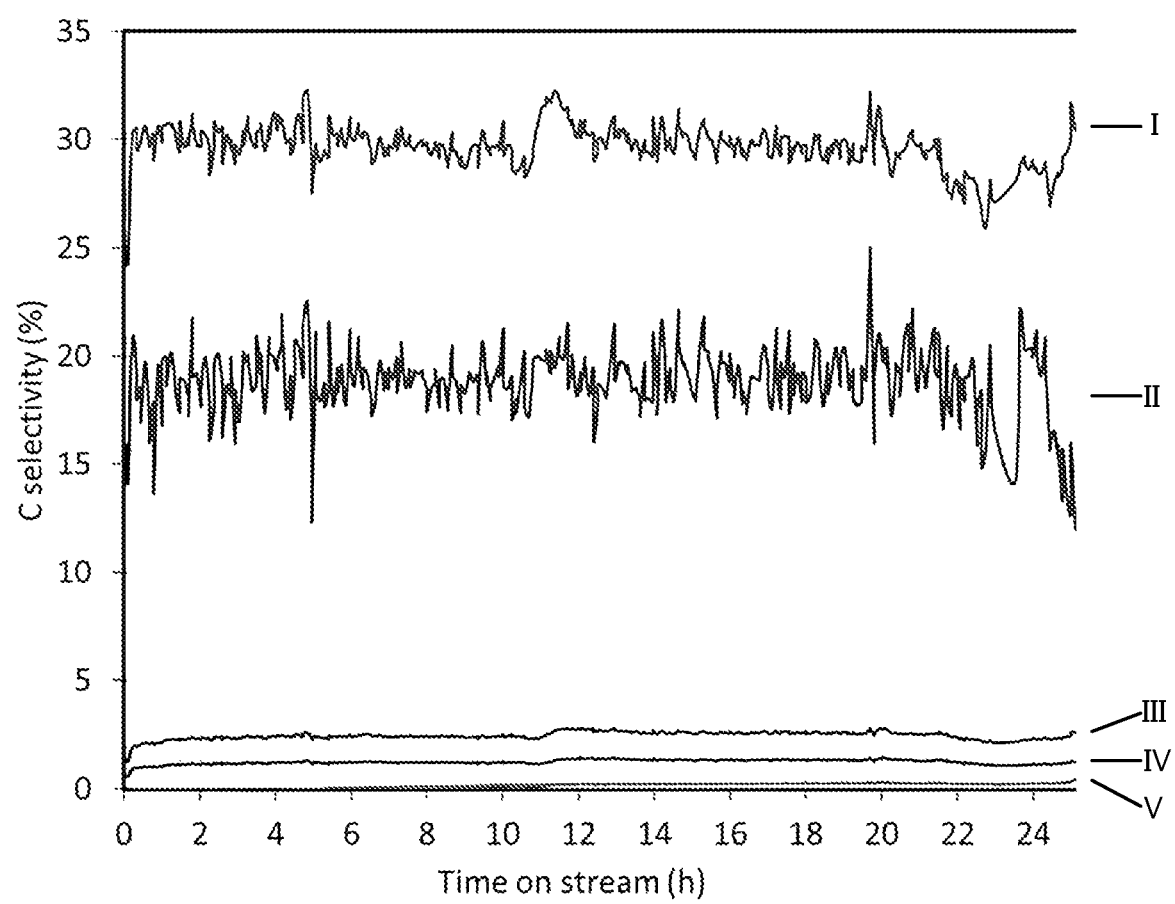
FIG. 15 depicts the carbon selectivities for toluene (I), benzene (II), m+p-xylene (III), o-xylene (IV) and ethylbenzene (V), as obtained in Example 4.

The Ga-ZSM-5 aromatization catalyst with a loading of about 2.5 wt %, synthesized and tested in Example 1, was re-used for a duration test for the determination of the long-term performance of the catalyst. All process steps and conditions (temperature, GHSV, gasification conditions) were the same as in Example 1. The catalyst was in operation for approximately 25 hours at a fixed temperature of 500° C. The catalyst performed stably over the entire run, with only a slight overall decrease in ethylene conversion. Ethylene conversion was about 95-97%. The carbon selectivity of ethylene and acetylene to aromatics was stable over the 25 hours of the duration test. The catalyst showed carbon selectivity to benzene of about 20%, and of about 30% to toluene. The carbon selectivity to xylenes was in comparison significantly lower than that of benzene and toluene (about 5% in total, with slightly higher selectivity to m- and p-xylene than to o-xylene). The catalyst showed negligible selectivity to ethylbenzene. These results are depicted in FIG. 15.

The inlet and outlet flows of the reactor were determined for ethylene, acetylene, ethane, benzene, toluene, ethylbenzene and xylene. Gas concentrations were measured during the entire run online by micro-GC (as in Example 1), and neon was added as tracer gas for the determination of molar balances around the reactor. All inlet and outlet flows remained stable for the entire run. The results are depicted in Table 7.

TABLE 7

Inlet and outlet concentrations of selected gas compounds (operation at 500° C.)

| Compound | Inlet gas concentration (on dry basis) | Outlet gas concentration (on dry basis) |
| --- | --- | --- |
| ethylene | 3.89 ± 0.04 vol. % | 0.17 ± 0.02 vol. % |
| acetylene | 0.37 ± 0.007 vol. % | <0.001 vol. % * |
| ethane | 0.24 ± 0.005 vol. % | 1.38 ± 0.08 vol. % |
| methane | 12.4 ± 0.13 vol. % | 13.4 ± 0.12 vol. % |
| benzene | 7554.5 ± 289.9 ppmv | 10607.7 ± 180.8 ppmv |
| toluene | 554.7 ± 27.9 ppmv | 4294.0 ± 118.0 ppmv |
| ethylbenzene | 19.1 ± 15.1 ppmv | 31.7 ± 5.4 ppmv |
| m/p-xylene | 14.6 ± 0.7 ppmv | 286.3 ± 19.7 ppmv |
| o-xylene | 6.4 ± 0.6 ppmv | 144.1 ± 11.6 ppmv |

* Detection limit of micro-GC

Ethylene was converted down to 0.2 vol. %, whereas acetylene was converted below detection limits. The concentration of ethane was slightly increased in the reactor, which was also the case for methane. Since ethane and methane are desirable components of (bio-)SNG, the process according to the invention was not only able to convert ethylene into useful monocyclic aromatic compounds, but also the yield of bio-SNG was increased. Benzene concentration was increased with 30%, while toluene outlet flow was 7 times as high as inlet flow. For the xylene isomers, the outlet flow was about 20 times higher as the inlet flows. On the contrary, the carbon selectivity of the catalyst to ethylbenzene was negligible. Carbon selectivity to xylenes and ethylbenzene was significantly favoured when operating at lower temperatures (data not shown).

Further, the ZSM-5 support was found to completely capture $H_2S$ and COS. The breakthrough of $H_2S$ took place almost 6 hours after the start of the run. However, the zeolite still retained certain capacity for sulphur capture, which gradually decreases over time. After 25 hours operation at 500° C., the zeolite still captured approximately half of the $H_2S$. The $N_2$ flush applied to the catalyst after 25 hours operation seemed to partially regenerate the zeolite. The zeolite support was also able to capture thiophene and mercaptan derivatives (not shown), which is beneficial for the purity of the liquid product containing the monocyclic aromatic compounds.

The invention claimed is:

1. A process for producing a fraction of monocyclic aromatic compounds from a product gas of a gasification process, comprising:
   (a) contacting the gas with a catalyst capable of converting ethylene into monocyclic aromatic compounds;
   (b) isolating monocyclic aromatic compounds from the gas originating from step (a).

2. The process according to claim 1, wherein the gasification process involves the gasification of coal, biomass or waste.

3. The process according to claim 1, wherein the isolating of step (b) is performed by
   (b1) contacting the gas originating from step (a) with a washing liquid, at a temperature of 15-60° C., to obtain the purified gas and a spent washing liquid;
   (b2) contacting the spent washing liquid with a stripping gas comprising steam, to obtain a loaded stripping gas comprising monocyclic aromatic compounds and a stripped washing liquid; and
   (b3) separating the monocyclic aromatic compounds from the loaded stripping gas obtained in step (b2) to obtain a composition comprising monocyclic aromatic compounds.

4. The process according to claim 3, wherein the stripping gas comprises at least 95 vol. % steam.

5. The process according to claim 3, wherein the process further comprises step (c) that involves condensation of the loaded stripping gas to obtain an immiscible liquid composition comprising water and monocyclic aromatic compounds, collection of the liquid composition in a vessel and liquid-liquid separation thereof.

6. The process according to claim 3, wherein the washing liquid comprises an organic polysiloxane.

7. The process according to claim 1, wherein the monocyclic aromatic compounds include one or more selected from benzene, toluene, xylenes and ethylbenzene.

8. The process according to claim 1, wherein the catalyst capable of converting ethylene into monocyclic aromatic compounds comprises a zeolite, wherein the zeolite is optionally a ZSM-5 zeolite, and wherein the zeolite is optionally promoted with Ga, Zn and/or Mo.

9. The process according to claim 1 any one of the preceding claims, wherein step (a) is performed at a temperature of 250-650° C.

10. The process according to claim 1, wherein the gas that is subjected to step (a) comprises ethylene and optionally at least one of (i) 5-30 vol % $CH_4$; (ii) 1-15 vol % $C_2H_x$, wherein x=2, 4 or 6; (iii) 1-10 vol. % $C_yH_z$, wherein y=3, 4 or 5 and z=(2y−2), (2y) or (2y+2); (iv) 10-60 vol % $H_2$; (v) 5-50 vol % CO; and (vi) 5-50 vol % $CO_2$, based on total dry volume.

11. The process according to claim 1, wherein tar-like components are removed from the gas prior to step (a), by:
   (c1) contacting the gas with a pre-washing liquid at a temperature of 60-150° C., to obtain a detarred gas which is fed to step (a) and a spent pre-washing liquid; and
   (c2) contacting the spent pre-washing liquid with a tar stripping gas, to obtain a loaded tar stripping gas and a stripped pre-washing liquid.

12. The process according to claim 1, wherein the gas is subjected to water removal prior to step (a), wherein the water removal is optionally conducted in a condenser.

13. A modular system for performing the process according to claim 1, comprising:
   (a) an ethylene conversion module for converting ethylene into monocyclic aromatic compounds, comprising a gas inlet (a1) for receiving the gas, a catalyst (a2) capable of converting ethylene into monocyclic aromatic compounds and a gas outlet (a3) for discharging a gas enriched in monocyclic aromatic compounds;
   (b1) an absorbing unit comprising a gas inlet (b11) for receiving the gas enriched in monocyclic aromatic compounds, a liquid inlet (b12) for receiving a washing liquid, a gas outlet (b14) for discharging a purified gas and a liquid outlet (b15) for discharging a spent washing liquid; and (b2) a stripping unit, comprising a liquid inlet (b21) for receiving the spent washing liquid, a gas inlet (b22) for receiving a stripping gas, a gas outlet (b23) for discharging a loaded stripping gas and a liquid outlet (b24) for discharging a stripped washing liquid, wherein outlet (a3) is in fluid connection with inlet (b11), outlet (b15) is in fluid connection with inlet (b21) and wherein outlet (b24) is optionally in fluid connection with inlet (b12).

14. The modular system according to claim 13, further comprising:

(b3) a separating module, comprising a gas inlet (b31) for receiving the loaded stripping gas, means (b32) for separating the monocyclic aromatic compounds from the stripping gas, an outlet (b33) for discharging a cleared stripping gas, and an outlet (b34) for discharging the monocyclic aromatic compounds, wherein outlet (b23) is in fluid connection with inlet (b31) and wherein outlet (b33) is optionally in fluid connection with inlet (b22).

15. The modular system according to claim 13, further comprising:

(c1) a pre-washing unit comprising a gas inlet (c11) for receiving a gas comprising tar-like components and monocyclic aromatic compounds, a liquid inlet (c12) for receiving a pre-washing liquid, a gas outlet (c14) for discharging a detarred gas and a liquid outlet (c15) for discharging a spent pre-washing liquid; and (c2) a tar stripping unit, comprising a liquid inlet (c21) for receiving the spent pre-washing liquid, a gas inlet (c22) for receiving a tar stripping gas, a gas outlet (c23) for discharging loaded tar stripping gas and a liquid outlet (c24) for discharging a stripped pre-washing liquid, wherein outlet (c14) is in fluid connection with inlet (al), outlet (ci5) is in fluid connection with inlet (c21) and wherein outlet (c24) is optionally in fluid connection with inlet (c12).

* * * * *